US012779104B2

(12) United States Patent
Combs et al.

(10) Patent No.: US 12,779,104 B2
(45) Date of Patent: Nov. 3, 2026

(54) LIQUID CONTAINER SYSTEM

(71) Applicant: GEN-PROBE INCORPORATED, San Diego, CA (US)

(72) Inventors: David H. Combs, San Diego, CA (US); Ayra A. Baker, Escondido, CA (US); Norbert D. Hagen, Carlsbad, CA (US); David A Buse, San Diego, CA (US)

(73) Assignees: Gen-Probe Incorporated, San Diego, CA (US); Grifols, S.A., Barcelona (ES)

( * ) Notice: Subject to any disclaimer, the term of this patent is extended or adjusted under 35 U.S.C. 154(b) by 0 days.

(21) Appl. No.: 18/655,093

(22) Filed: May 3, 2024

(65) Prior Publication Data

US 2024/0287981 A1 Aug. 29, 2024

Related U.S. Application Data

(63) Continuation of application No. 17/608,456, filed as application No. PCT/US2020/029238 on Apr. 22, 2020, now Pat. No. 12,006,930.

(60) Provisional application No. 62/842,974, filed on May 3, 2019.

(51) Int. Cl.
*A61M 1/00* (2006.01)

(52) U.S. Cl.
CPC .............. *A61M 1/784* (2021.05); *A61M 1/60* (2021.05); *A61M 1/631* (2021.05); *A61M 1/78* (2021.05)

(58) Field of Classification Search
CPC ........... A61M 1/60; A61M 1/78; A61M 1/631
See application file for complete search history.

(56) References Cited

U.S. PATENT DOCUMENTS

| | | | |
|---|---|---|---|
| 3,051,175 | A | 8/1962 | Nugent |
| 3,788,349 | A | 1/1974 | Meyer et al. |
| 3,863,634 | A | 2/1975 | Reynolds et al. |
| 4,228,798 | A | 10/1980 | Deaton |
| 4,487,606 | A | 12/1984 | Leviton et al. |
| 4,681,562 | A | 7/1987 | Beck et al. |
| 4,826,494 | A | 5/1989 | Richmond et al. |

(Continued)

FOREIGN PATENT DOCUMENTS

| | | |
|---|---|---|
| CN | 101025180 A | 8/2007 |
| CN | 101326107 A | 12/2008 |

(Continued)

OTHER PUBLICATIONS

APO Examination Report No. 1, Australian Application No. 2020268175, Mar. 3, 2025.
PCT International Search Report, International Application No. PCT/US2020/029238, Aug. 12, 2020.

(Continued)

*Primary Examiner* — Timothy L Maust
(74) *Attorney, Agent, or Firm* — Rothwell, Figg, Ernst & Manbeck, P.C.; Charles B. Cappellari

(57) ABSTRACT

A liquid container system having a liquid container, where the liquid container includes (i) an intermediate top wall, (ii) a liquid inlet tower extending above the intermediate top wall, (iii) a liquid inlet fluidly connected to the liquid inlet tower at a position above the intermediate top wall and through which the liquid container receives liquid from a liquid source, and (iv) a vacuum tower extending above the intermediate top wall and to which a pressure differential source can be fluidly connected at a position above the intermediate top wall to draw liquid into the liquid container through the liquid inlet.

14 Claims, 17 Drawing Sheets

(56) References Cited

U.S. PATENT DOCUMENTS

| | | | | |
|---|---|---|---|---|
| 4,886,504 | A | 12/1989 | Arvidson et al. | |
| 5,234,412 | A | 8/1993 | Forberg | |
| 5,255,720 | A | 10/1993 | McPherson | |
| 5,269,030 | A | 12/1993 | Pahno et al. | |
| 5,914,047 | A | 6/1999 | Griffiths | |
| 6,342,048 | B1 | 1/2002 | Verkaart et al. | |
| 6,652,495 | B1 | 11/2003 | Walker | |
| 7,469,727 | B2 * | 12/2008 | Marshall | A61M 1/60 604/326 |
| 7,611,500 | B1 | 11/2009 | Lina et al. | |
| 8,100,874 | B1 * | 1/2012 | Jordan | A61M 1/79 604/319 |
| 8,449,839 | B2 | 5/2013 | Rajagopal et al. | |
| 8,900,534 | B2 | 12/2014 | Daf | |
| 8,992,833 | B2 | 3/2015 | Blecka et al. | |
| 12,006,930 | B2 | 6/2024 | Combs et al. | |
| 2007/0044439 | A1 | 3/2007 | Dunn et al. | |
| 2009/0216205 | A1 | 8/2009 | Ryan et al. | |
| 2013/0134183 | A1 | 5/2013 | Van Diepen et al. | |
| 2016/0168777 | A1 | 6/2016 | Bison et al. | |
| 2017/0192030 | A1 | 7/2017 | Lapham et al. | |
| 2017/0239141 | A1 | 8/2017 | Davis et al. | |
| 2018/0126306 | A1 | 5/2018 | Wade et al. | |
| 2018/0172563 | A1 | 6/2018 | Durrant et al. | |
| 2018/0210002 | A1 | 7/2018 | Lapham et al. | |
| 2024/0280096 | A1 | 8/2024 | Combs et al. | |

FOREIGN PATENT DOCUMENTS

| | | | |
|---|---|---|---|
| CN | 102939035 | A | 2/2013 |
| CN | 104633369 | A | 5/2015 |
| CN | 105298856 | A | 2/2016 |
| CN | 106219473 | A | 12/2016 |
| CN | 205826365 | U | 12/2016 |
| CN | 108175881 | A | 6/2018 |
| EP | 0 411 620 | A2 | 2/1991 |
| EP | 1837045 | A1 | 9/2007 |
| EP | 2 762 887 | B1 | 2/2019 |
| JP | H10-151194 | A | 6/1998 |
| JP | H11-178915 | A | 7/1999 |
| JP | 2002045842 | A | 2/2002 |
| JP | 2010-513928 | A | 4/2010 |
| KR | 20180002239 | U | 7/2018 |
| KR | 10-2020-0000551 | U | 3/2020 |
| WO | 1993/012430 | A1 | 6/1993 |
| WO | 2006/043900 | A1 | 4/2006 |
| WO | 2008/079598 | A1 | 7/2008 |
| WO | 2009/033128 | A1 | 3/2009 |
| WO | 2009030118 | A1 | 3/2009 |
| WO | 2009/094761 | A1 | 8/2009 |
| WO | 2014/119399 | A1 | 8/2014 |
| WO | 2018/126098 | A1 | 7/2018 |

OTHER PUBLICATIONS

PCT International Preliminary Report on Patentability and Written Opinion of the International Searching Authority, International Application No. PCT/US2020/029238, Nov. 2, 2021.

CIPO Examination Report, Canadian Application No. 3,138,508, Jan. 3, 2023.

CIPO Examination Report, Canadian Application No. 3,138,508, Feb. 3, 2022.

CIPO Examination Report, Canadian Application No. 3,138,508, Jun. 22, 2022.

CIPO Examination Report, Canadian Application No. 3,205,268, Aug. 22, 2024.

CNIPA First Office Action, Chinese Application No. 202080044364.3, Mar. 31, 2023.

CNIPA Search Report, Chinese Application No. 202080044364.3, Mar. 28, 2023.

CNIPA Second Office Action, Chinese Application No. 202080044364.3, Oct. 20, 2023.

CNIPA Chinese Notice of Allowance with Search Report, Chinese Application No. 202080044364.3, Mar. 22, 2024.

CNIPA Notice of Allowance with Search Report and English translation in related Chinese patent application No. 202080044364.3, Mar. 22, 2024.

EPO Communication pursuant to Article 94(3) EPC, European Application No. 20725028.3, Mar. 1, 2023.

EPO Communication pursuant to Article 94(3) EPC, European Application No. 20725028.3, Dec. 1, 2023.

EPO Communication pursuant to Article 94(3) EPC, European Application No. 20725028.3, Jul. 2, 2024.

JPO Office Action, Japanese Patent Application No. 2021-564997, Mar. 1, 2023.

USPTO Non-Final Rejection, U.S. Appl. No. 17/608,456, filed Oct. 13, 2023.

USPTO Notice of Allowance, U.S. Appl. No. 17/608,456, filed Feb. 6, 2024.

Office Action issued in Chinese Patent Application No. 202410587831.7 dated Nov. 27, 2025 (14 pages).

CNIPA First Office Action, Chinese Application No. 202410587828.5, Nov. 4, 2025.

CNIPA Search Report, Chinese Application No. 202410587828.5, Nov. 3, 2025.

EPO Extended European Search Report, European Application No. 25204326.0, Dec. 11, 2025.

Examination Report received for Canadian Patent Application No. 3205268, mailed on Jan. 29, 2026, 05 pages.

Office Action received for U.S. Appl. No. 18/655,119, mailed on Mar. 27, 2026, 11 pages.

CNIPA, Second Office Action, Chinese Application No. 202410587828.5, May 1, 2026.

Notice of Allowance mailed on Jun. 30, 2026, in corresponding U.S. Appl. No. 18/655,119, 8 pages.

* cited by examiner

LIQUID CONTAINER SYSTEM

CROSS REFERENCE OF RELATED APPLICATION

This application is a divisional of U.S. application Ser. No. 17/608,456, filed Nov. 2, 2021, now U.S. Pat. No. 12,006,930, which is a national phase entry pursuant to 35 U.S.C. § 371 of International Application No. PCT/US2020/029238, filed Apr. 22, 2020, which claims the benefit under 35 U.S.C. § 119(c) of the filing date of U.S. Provisional Application No. 62/842,974, filed May 3, 2019, the disclosures of which applications are incorporated herein by reference.

FIELD OF THE DISCLOSURE

This disclosure relates to systems and methods for collecting and discarding liquid waste.

BACKGROUND

Certain instruments, such as diagnostic and clinical analyzers, perform processes in which liquid wastes are generated. Such liquid wastes must be managed—i.e., collected, temporarily stored, and then discarded-during and/or after operation of the instrument. Typically, such waste liquids are collected on the instrument in an on-board, liquid waste collection container (e.g., a bottle) and temporarily stored in the collection container. Such liquids may be collected from on-board sources, such as aspirators, drains, or the like.

Periodically, over the course of a sustained operation of the instrument, the liquid waste collection container must be emptied, or replaced with an empty collection container, as the container becomes filled with collected waste liquids. Typically, the liquid waste container is emptied by removing it from the instrument to empty the contents of the collection container or to replace the full container with an empty one. During the time that the liquid waste collection container is removed from the instrument, however, operation of the instrument must be suspended, as there is no container to collect liquid wastes. Having to suspend operation of the instrument each time a liquid waste collection container must be emptied or replaced can have a negative impact on the instrument's throughput.

SUMMARY

The following presents a simplified summary in order to provide a basic understanding of some aspects described herein. This summary is not an extensive overview of the claimed subject matter. It is intended to neither identify key or critical elements of the claimed subject matter nor delineate the scope thereof. Its sole purpose is to present some concepts in a simplified form as a prelude to the more detailed description that is presented later.

Aspects of the disclosure are embodied in system for managing liquid waste. The system may include a first liquid container configured to receive liquid from a liquid source, a liquid transfer pump fluidly connected to the first liquid container, and a second liquid container fluidly connectable to the liquid transfer pump. The liquid transfer pump is configured to be selectively activated to transfer liquid from the first liquid container to the second liquid container when the second liquid container is fluidly connected to the liquid transfer pump.

According to other aspects, the system may further include a pressure differential source to which the first liquid container is connected to draw liquid into the first liquid container from the liquid source.

According to other aspects, the pressure differential source may include a vacuum pump.

According to other aspects, the system may further include a filter between the vacuum pump and the first liquid container.

According to other aspects, the filter may include a bleach fume filter.

According to other aspects, the system may further include a mounting block on which the filter and the first liquid container are mounted.

According to other aspects, the system may further include a filter loop fluidly connecting a top portion of the first liquid container to a bottom portion of the filter supported on the mounting block.

According to other aspects, the first liquid container may include an intermediate top wall, a first tower extending above the intermediate top wall, and a second tower extending above the intermediate top wall. The first tower includes a liquid inlet in the first tower for receiving liquid from the liquid source into the first liquid container, and the second tower includes a vacuum fitting in the second tower to which the vacuum pump is attached to draw liquid into the first liquid container from the liquid source.

According to other aspects, the liquid transfer pump may include a bellows pump.

According to other aspects, the system may further include a motor for operating the liquid transfer pump and a transmission coupling the motor to the liquid transfer pump.

According to other aspects, the system may further include a poppet valve associated with the second liquid container for controlling liquid flow into the second liquid container.

According to other aspects, the system may further include a float switch within the first liquid container, where the float switch is in communication with the liquid transfer pump to activate the liquid transfer pump when liquid within the first liquid container reaches a predefined level.

According to other aspects, the system may further include a connector fitting for fluidly connecting the second liquid container to the liquid transfer pump and a drip management system configured to draw liquid from the connector fitting into the first liquid container.

According to other aspects, the system may further include a connector fitting for fluidly connecting the second liquid container to the liquid transfer pump, a drip management system configured to draw liquid from the connector fitting into the first liquid container, and a vacuum pump to which the first liquid container is connected to draw liquid into the first liquid container from the liquid source. The connector fitting may include a female connector member and a male connector member received within the female connector member. The drip management system may include a connection port in communication with the female connector member, a fluid conduit connecting the connection port to the first liquid container, and a drip control valve, where the drip control valve is configured to permit fluid flow through the fluid conduit when the drip control valve is in an open configuration and to prevent fluid flow through the fluid conduit when the drip control valve is in a closed configuration.

According to other aspects, the drip control valve is a solenoid valve.

According to other aspects, the drip control valve is configured and controlled to be in the open configuration after the liquid transfer pump is deactivated following a transfer of liquid from the first liquid container to the second liquid container.

According to other aspects, the drip control valve is configured and controlled to be in the open configuration for a prescribed period of time after the liquid transfer pump is deactivated following the transfer of liquid from the first liquid container to the second liquid container and to be in the closed configuration all other times.

According to other aspects, the second liquid container includes a main body, a connector shelf extending laterally from the main body and including a horizontal portion and defining a bottom wall, and a liquid transfer connector fitting extending downwardly from the bottom wall of the horizontal portion of the connector shelf for fluidly connecting the second liquid container to the liquid transfer pump.

According to other aspects, the system may further include a connector interface fluidly connected to the liquid transfer pump and including an upwardly facing liquid connector fitting configured to be operably coupled to the downwardly extending liquid transfer connector fitting of the second liquid container to fluidly connect the liquid transfer pump to the second liquid container.

According to other aspects, the system may further include a liquid tray formed in the connector interface and surrounding the upwardly facing liquid connector fitting of the connector interface.

According to other aspects, the system may further include a drip management system configured to draw liquid from the liquid tray to the first liquid container or from the operably coupled liquid transfer connector fittings of the connector interface and the second liquid container to the first liquid container.

According to other aspects, the drip management system may include a connection port attached to the connector interface, a fluid conduit connecting the connection port to the first liquid container, and drip control valve. The drip control valve is configured to permit fluid flow through the fluid conduit when the drip control valve is in an open configuration and to prevent fluid flow through the fluid conduit when the drip control valve is in a closed configuration.

According to other aspects, the drip control valve is a solenoid valve.

According to other aspects, the drip control valve is configured and controlled to be in the open configuration when the liquid transfer pump is deactivated following a transfer of liquid from the first liquid container to the second liquid container.

According to other aspects, the drip control valve is configured and controlled to be in the open configuration for a prescribed period of time after the liquid transfer pump is deactivated following the transfer of liquid from the first liquid container to the second liquid container and to be in the closed configuration all other times.

According to other aspects, the system may further include a drain line connected to the second liquid container, and a drain pump fluidly connected to the drain line for transferring liquid from the second liquid container to a drain via the drain line.

According to other aspects, the system may further include a second float switch within the second liquid container, wherein the second float switch is in communication with the drain pump to activate the drain pump when liquid within the second liquid container reaches a predefined level.

According to other aspects, the system may further include a leak detection sensor.

According to other aspects, the first and second liquid containers and the liquid transfer pump are supported in a drawer of an instrument, and the drawer is configured to be laterally movable between an open position providing access to one or more of the first and second liquid containers and the liquid transfer pump and a closed position concealing the first and second liquid containers and the liquid transfer pump.

According to other aspects, the connector interface is affixed to the drawer.

According to other aspects, the first liquid container comprises an intermediate top wall, a liquid inlet tower extending above the intermediate top wall, a liquid inlet fluidly connected to the liquid inlet tower at a position above the intermediate top wall and through which the first liquid container receives liquid from the liquid source, and a vacuum tower extending above the intermediate top wall, and the pressure differential source is connected to the vacuum tower at a position above the intermediate top wall.

Further aspects of the disclosure are embodied in a method for managing liquid waste, the method comprising a) receiving liquid from a liquid source into a first liquid container, b) monitoring the amount of liquid in the first liquid container, c) connecting a second liquid container to a liquid transfer pump that is connected to the first liquid container by lowering a first connector fitting of the second liquid container into connective engagement with a second connector fitting coupled to an outlet of the liquid transfer pump, d) after the amount of liquid received into the first liquid container reaches a predefined level, as determined in step b), transferring liquid from the first liquid container into the second liquid container with the liquid transfer pump, and e) removing liquid transferred to the second liquid container during step d).

According to other aspects, step e) comprises transferring liquid from the second liquid container to a drain with a drain pump fluidly connected to the second liquid container.

According to other aspects, step e) further comprises monitoring a liquid level within the second liquid container with a second float switch, generating a pump activation signal when the second float switch detects that the amount of liquid within the second liquid container reaches a predefined level, and transmitting the pump activation signal to the drain pump to activate the drain pump and transfer liquid from the second liquid container to the drain.

According to other aspects, the method may further include, prior to step e), deactivating the liquid transfer pump.

According to other aspects, step e) comprises pouring liquid from the second liquid container through an opening in the second liquid container.

According to other aspects, steps a) and e) occur simultaneously.

According to other aspects, the first and second liquid containers and the liquid transfer pump are supported in a drawer of an instrument. The drawer is configured to be laterally movable between an open position providing access to one or more of the first and second liquid containers and the liquid transfer pump and a closed position concealing the first and second liquid containers and the liquid transfer pump, and step e) further comprises laterally moving the drawer to the open position and removing the second liquid container from the drawer after deactivating liquid transfer pump.

According to other aspects, the first connector fitting may include a male fitting extending downwardly from the second liquid container, and the second connector fitting comprises an upwardly facing female fitting and configured to receive the male fitting.

According to other aspects, step b) comprises monitoring a liquid level within the first liquid container with a float switch, step c) comprises generating a pump activation signal when the float switch detects that the amount of liquid within the first liquid container reaches the predefined level, and transmitting the pump activation signal to the liquid transfer pump to activate the liquid transfer pump and transfer liquid from the first liquid container to the second liquid container.

According to other aspects, the method may further include, after step d) and before step e), drawing liquid from the connection between the first connector fitting and the second connector fitting into the first liquid container.

Further aspects of the disclosure are embodied in a liquid container system comprising a liquid container that includes an intermediate top wall, a liquid inlet tower extending above the intermediate top wall, a liquid inlet fluidly connected to the liquid inlet tower at a position above the intermediate top wall and through which the liquid container receives liquid from a liquid source, and a vacuum tower extending above the intermediate top wall and to which a pressure differential source can be fluidly connected at a position above the intermediate top wall to draw liquid into the liquid container through the liquid inlet.

According to other aspects, the liquid container system may further include a filter in fluid communication with the vacuum tower of the liquid container.

According to other aspects, the liquid container system may further include a mounting block on which the filter and the liquid container are mounted.

According to other aspects, the liquid container system may further include a filter loop fluidly connecting the vacuum tower of the liquid container to a bottom portion of the filter supported on the mounting block.

According to other aspects, the liquid container system may further include a liquid level sensor configured to detect a liquid level within the liquid container.

According to other aspects, the liquid level sensor may include a float switch extending into an interior of the liquid container from a float switch connector mounted to the intermediate top wall.

According to other aspects, the liquid container system may further include a transfer fitting mounted in the intermediate top wall with a tube extending from the transfer fitting into an interior of the liquid container.

According to other aspects, the liquid container system may further include a transfer line fitting mounted in the intermediate top wall with a tube extending from the transfer line fitting into an interior of the liquid container, a transfer pump fluidly connected to the transfer fitting, and a transfer container fluidly connected to the transfer pump.

According to other aspects, the liquid container system may further include a liquid level sensor configured to detect a liquid level within the liquid container, the liquid level sensor being in operative communication with the transfer pump to activate the transfer pump to transfer an amount of liquid from the liquid container to the transfer container when the liquid level sensor detects that the liquid level within the liquid container has reached a prescribed level.

According to other aspects, the liquid container system may further include a transfer container interface configured to releasably connect the transfer container to the transfer pump.

According to other aspects, the transfer container may include a main body, a connector shelf extending laterally from the main body and including a horizontal portion and defining a bottom wall, and a liquid transfer connector fitting extending downwardly from the bottom wall of the horizontal portion of the connector shelf and configured for fluidly connecting the transfer container to the liquid transfer pump.

According to other aspects, the liquid transfer connector fitting may include a nipple that extends downwardly from the horizontal portion of the connector shelf and a liquid channel extending through the liquid transfer connector fitting.

According to other aspects, the liquid container system may further include a transfer container interface configured to releasably connect the transfer container to the transfer pump, the transfer container interface including an upwardly facing receptor opening configured to receive the nipple of the liquid transfer connector fitting.

According to other aspects, the transfer container interface may include a liquid trough, and the receptor opening is disposed within the liquid trough.

According to other aspects, the liquid container system may further include one or more O-rings disposed on the nipple.

According to other aspects, the transfer container further includes a cap removably secured to an opening formed in the main body of the transfer container, wherein the opening is configured for emptying the contents of the transfer container after removing the cap.

According to other aspects, the transfer container may further include a handle secured to the main body.

Further aspects of the disclosure are embodied in a liquid container system comprising a transfer container for receiving liquid transferred to the transfer container by a liquid transfer pump. The transfer container may include a main body, a connector shelf extending laterally from the main body and including a horizontal portion and defining a bottom wall, and a liquid transfer connector fitting extending downwardly from the bottom wall of the horizontal portion of the connector shelf and configured for fluidly connecting the transfer container to the liquid transfer pump.

According to other aspects, the liquid transfer connector fitting may include a nipple that extends downwardly from the horizontal portion of the connector shelf and a liquid channel extending through the liquid transfer connector fitting.

According to other aspects, the liquid container system may further include a transfer container interface configured to releasably connect the transfer container to the transfer pump, the transfer container interface including an upwardly facing receptor opening configured to receive the nipple of the liquid transfer connector fitting.

According to other aspects, the transfer container interface includes a liquid trough, and the receptor opening is disposed within the liquid trough.

According to other aspects, the liquid container system may further include one or more O-rings disposed on the nipple.

According to other aspects, the transfer container further comprises a cap removably secured to an opening formed in the main body of the transfer container, and the opening is configured for emptying the contents of the transfer container after removing the cap.

According to other aspects, the transfer container further comprises a handle secured to the main body.

Other features and characteristics of the subject matter of this disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

The accompanying drawings, which are incorporated herein and form part of the specification, illustrate various embodiments of the subject matter of this disclosure. In the drawings, like reference numbers indicate identical or functionally similar elements.

DETAILED DESCRIPTION

Figure 1:
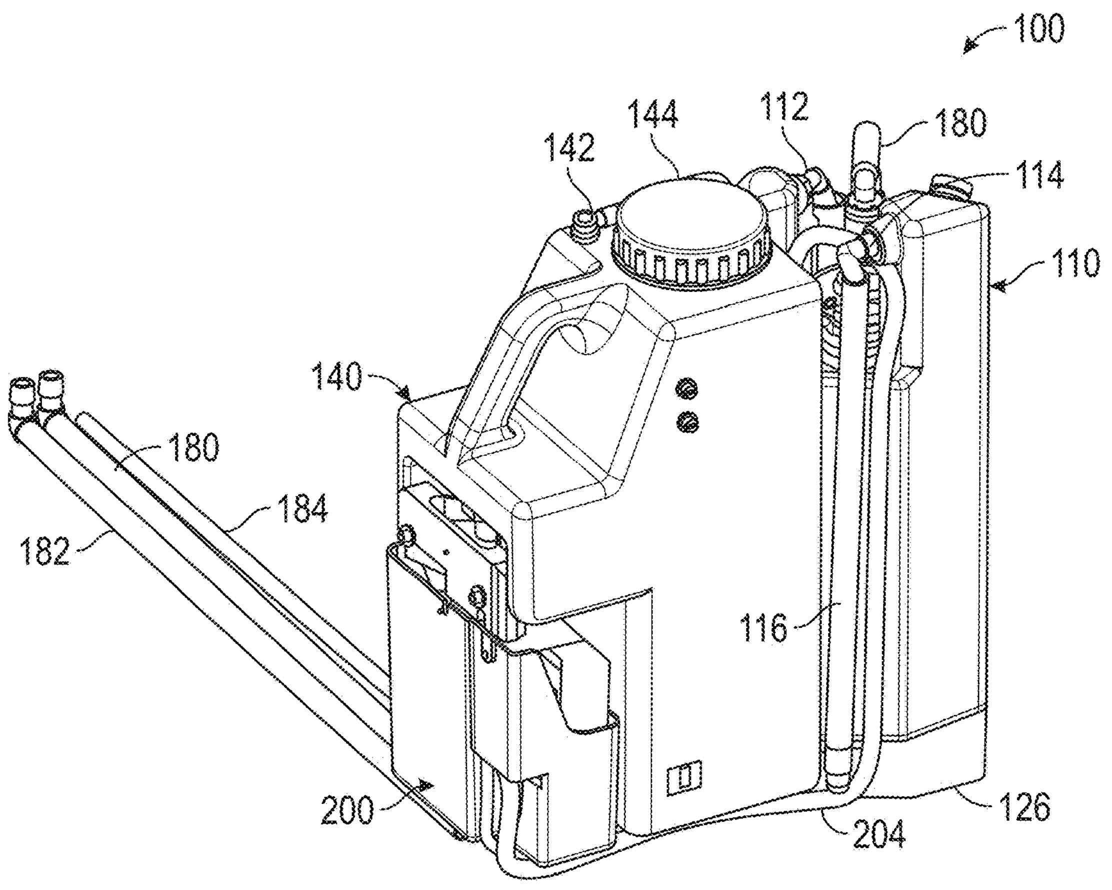
FIG. 1 is a perspective view of an implementation of a liquid waste management system as disclose herein.

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Unless defined otherwise, all terms of art, notations and other technical terms or terminology used herein have the same meaning as is commonly understood by one of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

Unless otherwise indicated or the context suggests otherwise, as used herein, "a" or "an" means "at least one" or "one or more."

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, over, under, on top of, upper, lower, left of, right of, in front of, behind, next to, adjacent, between, horizontal, vertical, diagonal, longitudinal, transverse, radial, axial, etc., are used for convenience in referring to such component, apparatus, location, feature, or a portion thereof in the drawings and are not intended to be limiting.

Furthermore, unless otherwise stated, any specific dimensions mentioned in this description are merely representative of an exemplary implementation of a device embodying aspects of the disclosure and are not intended to be limiting.

The use of the term "about" applies to all numeric values specified herein, whether or not explicitly indicated. This term generally refers to a range of numbers that one of ordinary skill in the art would consider as a reasonable amount of deviation to the recited numeric values (i.e., having the equivalent function or result) in the context of the present disclosure. For example, and not intended to be limiting, this term can be construed as including a deviation of ±10 percent of the given numeric value provided such a deviation does not alter the end function or result of the value. Therefore, under some circumstances as would be appreciated by one of ordinary skill in the art a value of about 1% can be construed to be a range from 0.9% to 1.1%.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "substantially" and "substantial" refer to a considerable degree or extent. When used in conjunction with, for example, an event, circumstance, characteristic, or property, the terms can refer to instances in which the event, circumstance, characteristic, or property occurs precisely as well as instances in which the event, circumstance, characteristic, or property occurs to a close approximation, such as accounting for typical tolerance levels or variability of the embodiments described herein.

As used herein, the terms "optional" and "optionally" mean that the subsequently described, component, structure, element, feature, event, circumstance, characteristic, property, etc. may or may not be included or occur and that the description includes instances where the component, structure, element, feature, event, circumstance, characteristic, property, etc. is included or occurs and instances in which it is not or does not.

The terms "fluid communication," "fluid connection," "fluidly connected," and similar terms mean either direct fluid communication or connection, for example, two regions can be in fluid communication with each other via an unobstructed fluid passageway capable of fluid transmission (e.g., channel, conduit, pipe, tube, hose, etc.) connecting the two regions or can be capable of being in fluid communication or connection, for example, two regions can be capable of fluid communication with each other when they are connected via a fluid passageway capable of fluid transmission that may include a valve disposed therein, wherein fluid communication can be established between the two regions upon actuating the valve. Fluid communication or connection between two regions is not limited to a condition of actual fluid flow between the two regions.

The term "line" when used in reference to a component for transmitting a liquid from one component or location to another component or location that is spatially distinct from the first component or location means any component so capable of such transmission, including, for example, a rigid or flexible conduit, channel, pipe, tube, hose, or combination of two or more thereof.

Figure 13:
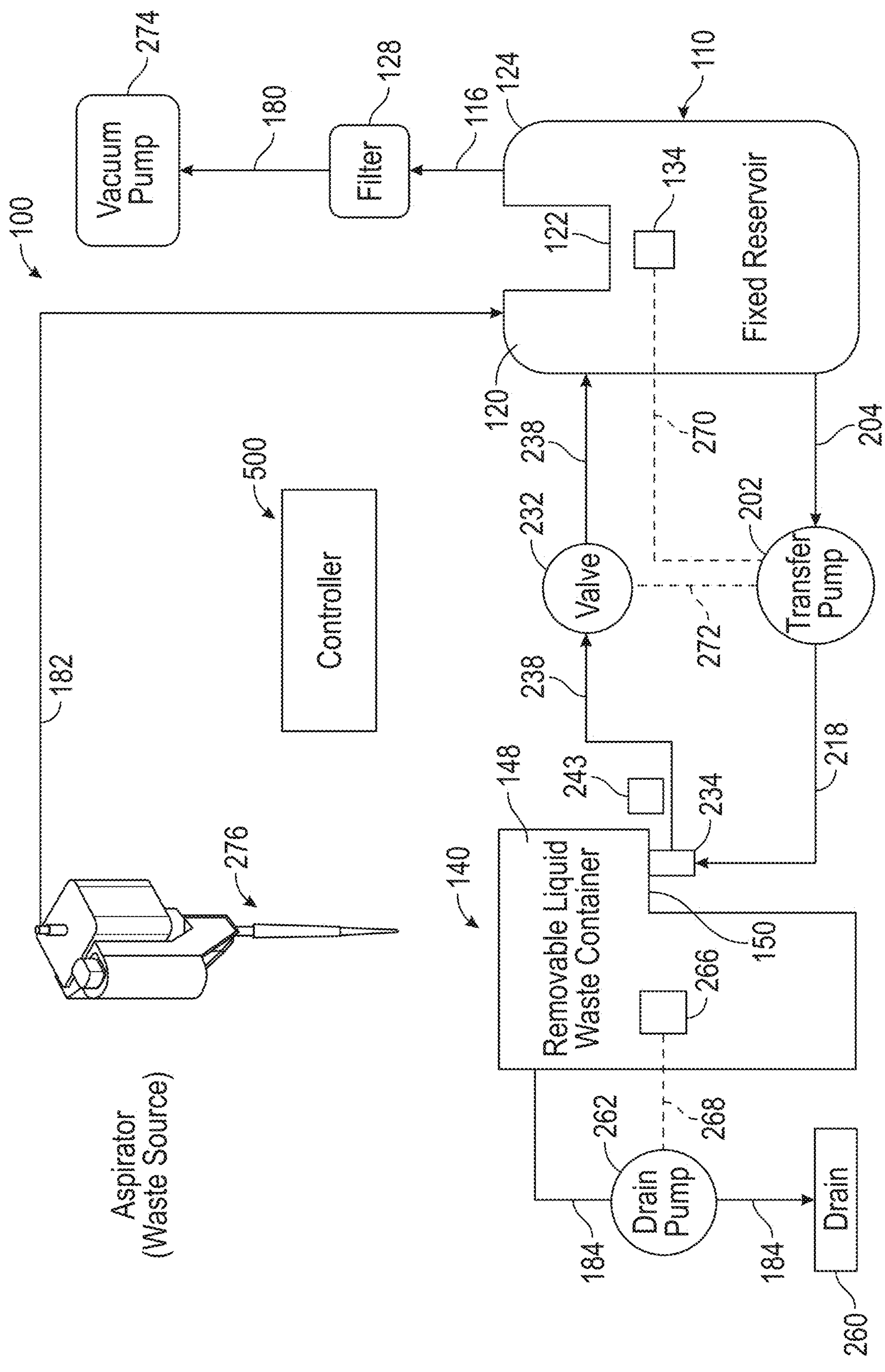
FIG. 13 is a schematic, block diagram of an embodiment of the liquid waste management system.

A liquid waste management system as disclosed herein is indicated by reference number 100 in FIG. 1 and FIG. 13. FIG. 13 represents a schematic, generalized block diagram illustrating various components of the system 100, and FIG. 1 illustrates a particular implementation of the system 100.

Figure 3:
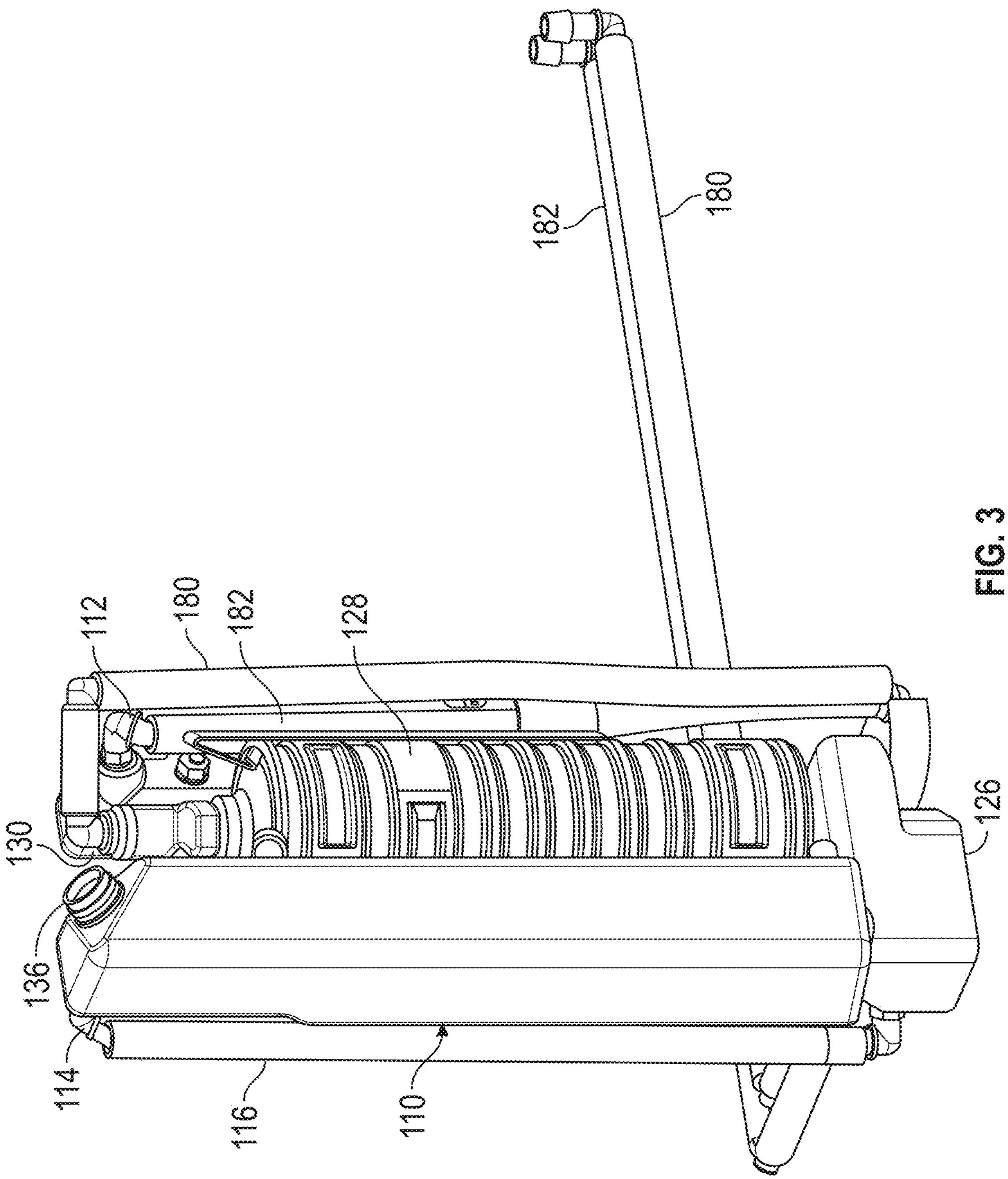
FIG. 3 is a rear perspective view of the vacuum reservoir of the liquid waste management system.

In various embodiments, system 100 includes a vacuum reservoir 110 (a first liquid container that is typically not removed or is not readily removable from the system 100) and a removable transfer container 140 (a second liquid container that may be removable from the system 100). Vacuum reservoir 110 and transfer container 140 may each be a rotomolded bottle manufactured from low-density polyethylene (LDPE). System 100 further includes a transfer pump module 200 including a pump (described in more detail below) that transfers liquid from vacuum reservoir 110 to transfer container 140 via a transfer line 204 (e.g., PVC tubing). Vacuum reservoir 110 is connected in line with a vacuum, or other pressure differential, via a vacuum line 180 and a vacuum filter loop (line) 116 through a filter 128 (see FIG. 3). Waste liquid is drawn into vacuum reservoir 110 from a waste liquid source 276 through a liquid waste inlet line 182 (e.g., PVC tubing) connected to vacuum reservoir 110.

Figure 14:
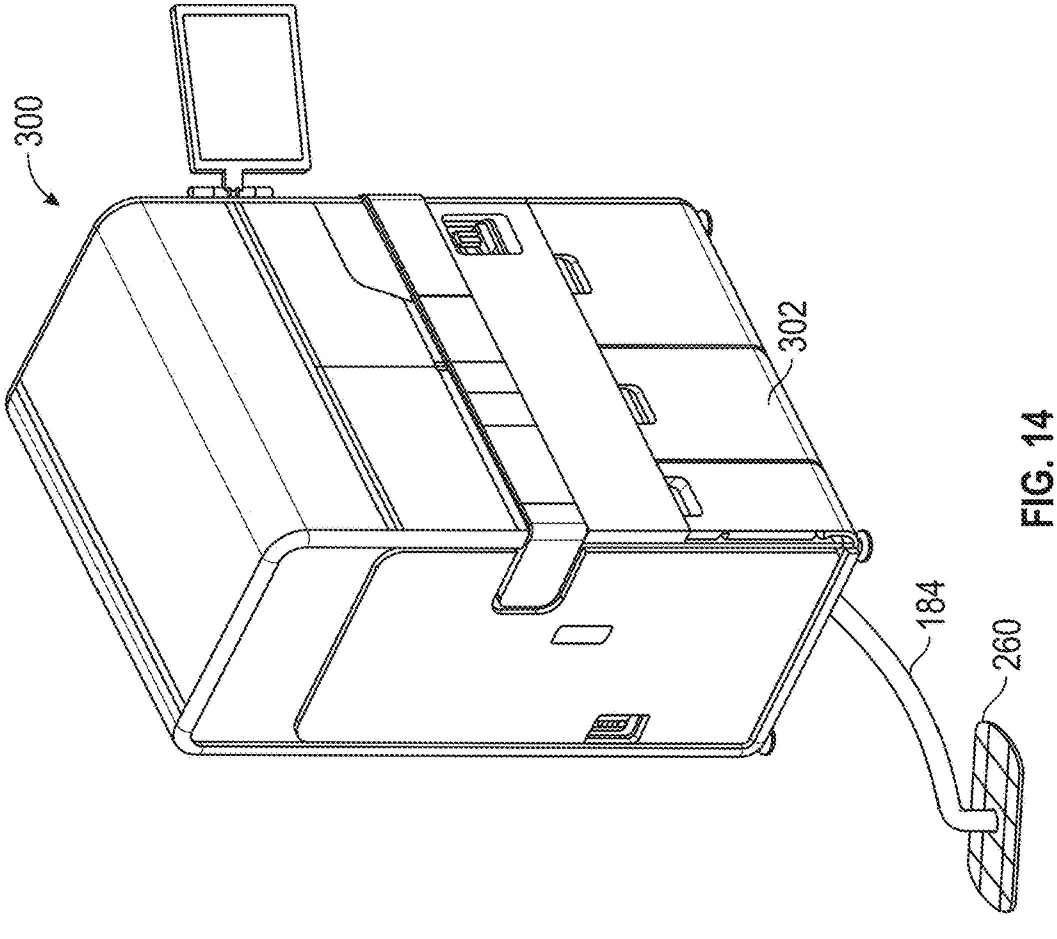
FIG. 14 is a perspective view of an exemplary processing instrument in which the liquid waste management system may be incorporated.
Figure 15:
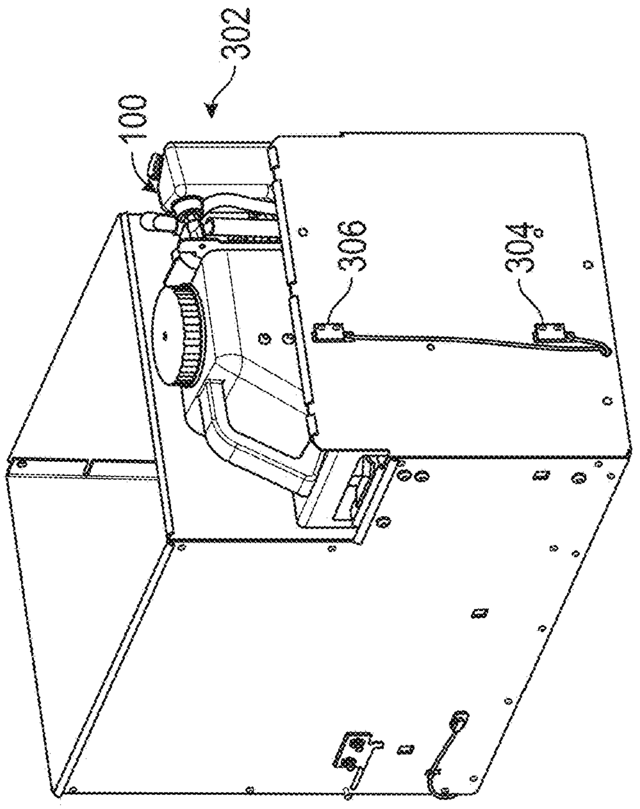
FIG. 15 is a perspective view of a drawer of the exemplary processing instrument in which the liquid waste management system may be supported.

As shown in FIGS. 14 and 15, and still referring to FIG. 1, components of the system 100, such as vacuum reservoir 110, transfer container 140, and transfer pump module 200 may be supported on a shelf or a movable drawer 302 of a processing instrument 300. In FIG. 15, a front panel with a handle on a front wall of the drawer is omitted from the drawing. Processing instrument 300 may be a chemical or biological analyzer, such as a molecular analyzer for performing nucleic acid-based amplification reactions. Exemplary processing instruments in which system 100 may be incorporated include analyzers described in U.S. Pat. Nos. 8,731,712 and 9,732,374 and International Publication No. WO 2019/014239 A1, as well as the Panther® and Panther Fusion® systems available from Hologic, Inc. (Marlborough, MA). In an embodiment, as liquid is transferred from vacuum reservoir 110 to transfer container 140, transfer container 140 can be periodically removed from the system 100 to be emptied, without disconnecting vacuum reservoir 110 from either the vacuum line 180 or the liquid waste inlet line 182. Accordingly, while transfer container 140 is removed from the system 100 to be emptied, vacuum reservoir 110 can continuously receive liquid waste via the liquid waste inlet line 182, and operation of the processing instrument 300 need not be interrupted.

As shown in FIGS. 1, 13, and 14, system 100 may optionally include a drain line 184 connected to transfer container 140 and coupled to a pump 262 for periodically drawing liquid from transfer container 140 to a drain 260 or bulk storage container, so as to reduce or eliminate the need to remove transfer container 140 for emptying.

Figure 2:
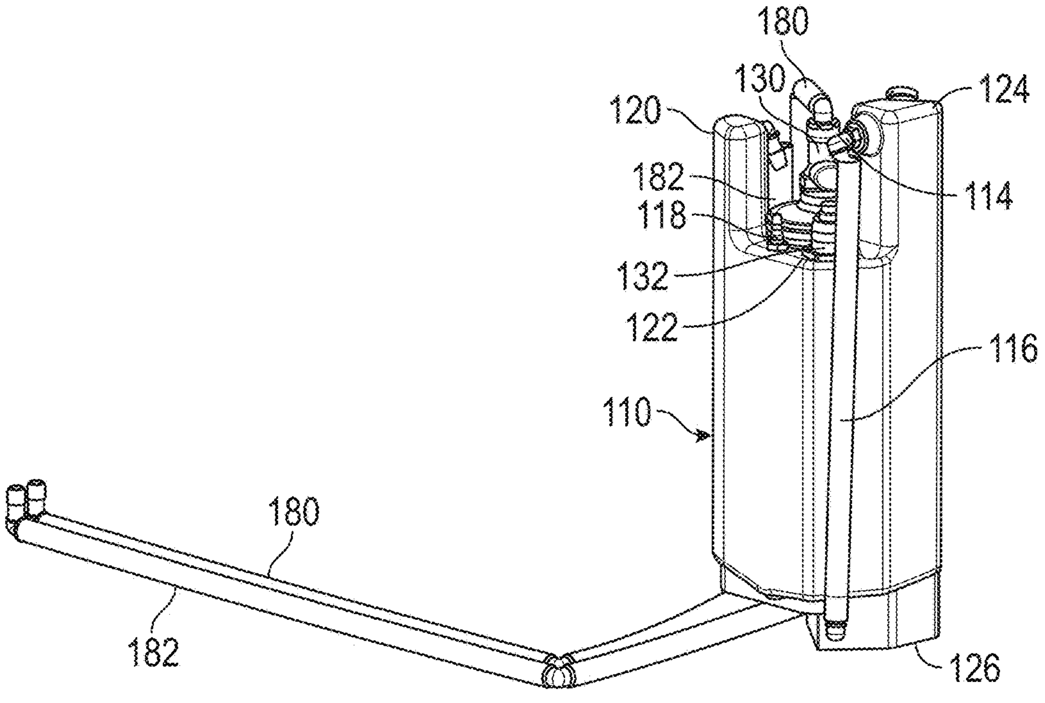
FIG. 2 is a front perspective view of a vacuum reservoir of the liquid waste management system.
Figure 4:
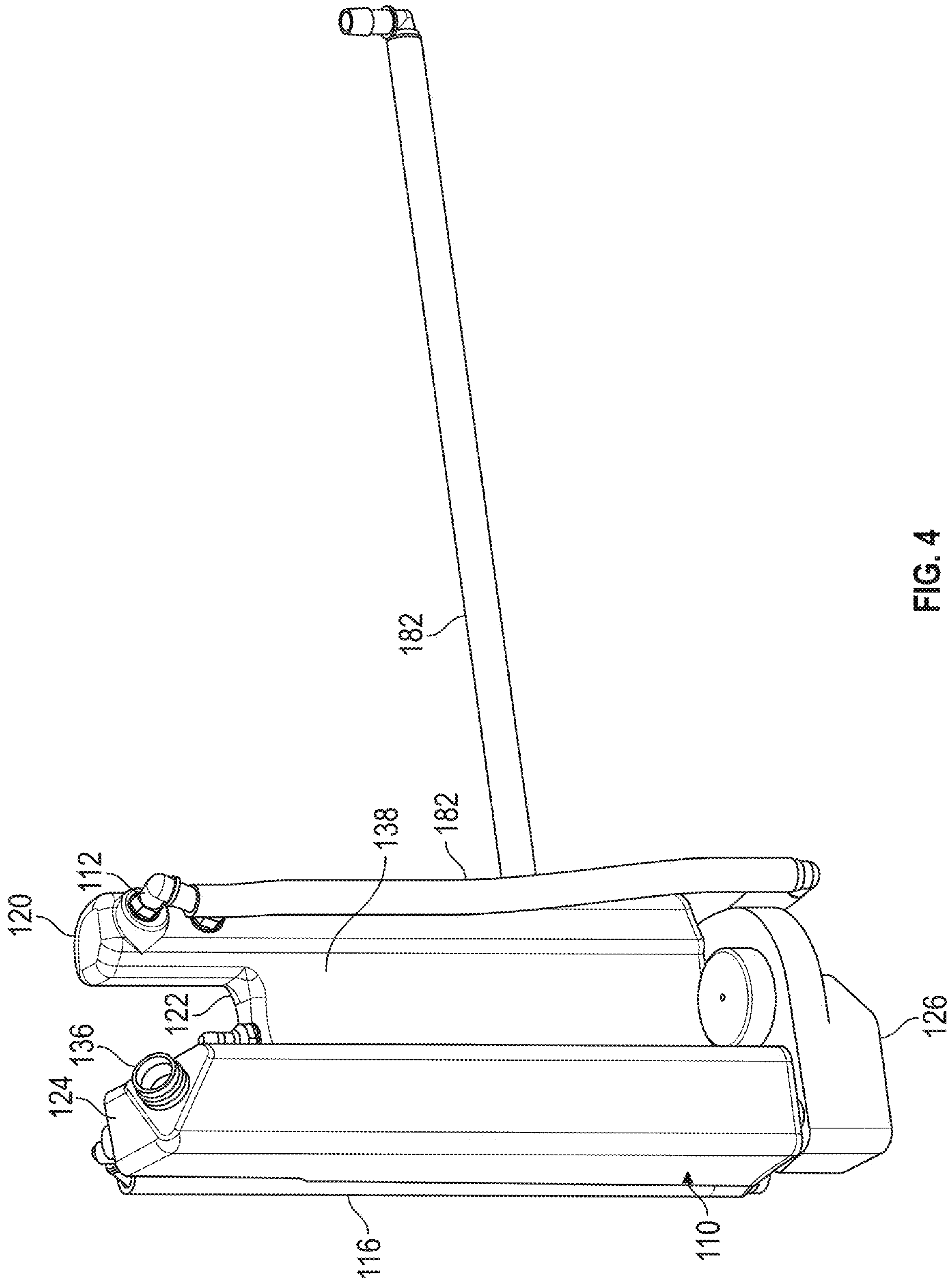
FIG. 4 is a rear perspective view of the vacuum reservoir of the liquid waste management system, with a filter omitted from the figure.

Vacuum reservoir 110 may be configured with a non-uniform top surface. As shown in FIG. 2, for example, in various embodiments, vacuum reservoir 110 includes an intermediate top wall 122 with a liquid inlet tower (or first tower) 120 and a vacuum tower (or second tower) 124 extending above the intermediate top wall 122. Liquid waste inlet line 182 is connected to the liquid inlet tower 120 at a waste inlet fitting 112 (see FIGS. 3 and 4). Waste inlet fitting 112 may comprise a right angle, barbed fitting with NPT (National Pipe Taper) threads. Waste inlet fitting 112 is preferably formed from a bleach compatible material, such as PP, PVDF, etc. Alternatively, waste inlet fitting 112 may be a quick connect fitting. Vacuum filter loop 116 is connected to vacuum tower 124 at a vacuum fitting 114 and extends into a filter mounting block 126, which supports filter 128 (see FIG. 3) nestled against a concave wall 138 (see FIGS. 4 and 8) formed on one side of vacuum reservoir 110. One end of filter 128 is in fluid communication with vacuum filter loop 116 through filter mounting block 126, and vacuum line 180 is connected to an opposite end of filter 128 at a filter outlet fitting 130. Vacuum filter loop 116 comprises tubing (e.g., PVC) that pulls air through the top of the vacuum reservoir 110. To pull vacuum through the vacuum reservoir 110 without liquid getting into vacuum line 180, vacuum loop 116 is connected to vacuum reservoir 110 at vacuum tower 124 to prevent fluid from entering filter loop 116. Vacuum fitting 114 may comprise a right angle, barbed fitting with NPT (National Pipe Taper) threads. Vacuum fitting 114 is preferably formed from a bleach compatible material, such as PP, PVDF, etc. Alternatively, vacuum fitting 114 may be a quick connect fitting.

Filter 128 has a specific orientation that requires flow to enter from a bottom side inlet at the filter mounting block 126. In an embodiment, filter mounting block 126 is a machined PVC block that is mounted to the bottom of the waste drawer 302. Filter mounting block 126 provides an airflow path from the vacuum fitting 114 connected to vacuum reservoir 110 to the filter 128. Mounting block 126 provides a mating surface to incorporate filter 128 into system 100. In an embodiment, filter 128 has an inlet and an outlet, and both sides have a male connection to fit a quick disconnect fitting. Mounting block 126 preferably interfaces with filter 128 to create an airtight seal between block 126 and filter 128, and filter 128 can be installed/removed by connecting/disconnecting filter outlet fitting 130. Filter 128 can be pulled upward and will disconnect from the mounting block 126. In an embodiment, filter 128 comprises a bleach fume filter. In an embodiment, filter 128 is a capsule with male fitting connections at both ends, such as connections available from CPC, St. Paul, MN. A bottom portion of the capsule houses a chemical media in pellet form that filters out the smell of bleach from the exhaust. A top portion of the capsule houses a 0.2 μm PTFE filter.

The vacuum tower 124 includes a threaded opening 136 at its upper surface configured to receive a mating threaded cap (not shown). Opening 136 is a service opening that allows a field service engineer (FSE) to see into the vacuum reservoir when troubleshooting. The FSE could pour liquid (water or endozime, etc.) to flush out the reservoir or test that the liquid level sensor float is working properly.

A vacuum from a vacuum source, such as a vacuum pump, is applied to vacuum reservoir 110 at the vacuum tower 124 by vacuum line 180 through the filter 128, filter mounting block 126, and vacuum filter loop 116. Thus, liquid waste from a liquid waste source is drawn through the liquid waste inlet line 182 into vacuum reservoir 110 at the liquid inlet tower 120. Liquid inlet tower 120 and the vacuum tower 124 disposed above the intermediate top wall 122 aid in limiting or preventing foam being sucked through the vacuum from vacuum reservoir 110.

A float switch connector 132 (see FIGS. 2, 5, 5A, and 8) mounted to the intermediate top wall 122 connects to a float switch 134 (continuous liquid level sensor) extending below the intermediate top wall 122 into the interior of vacuum reservoir 110.

Figure 5:
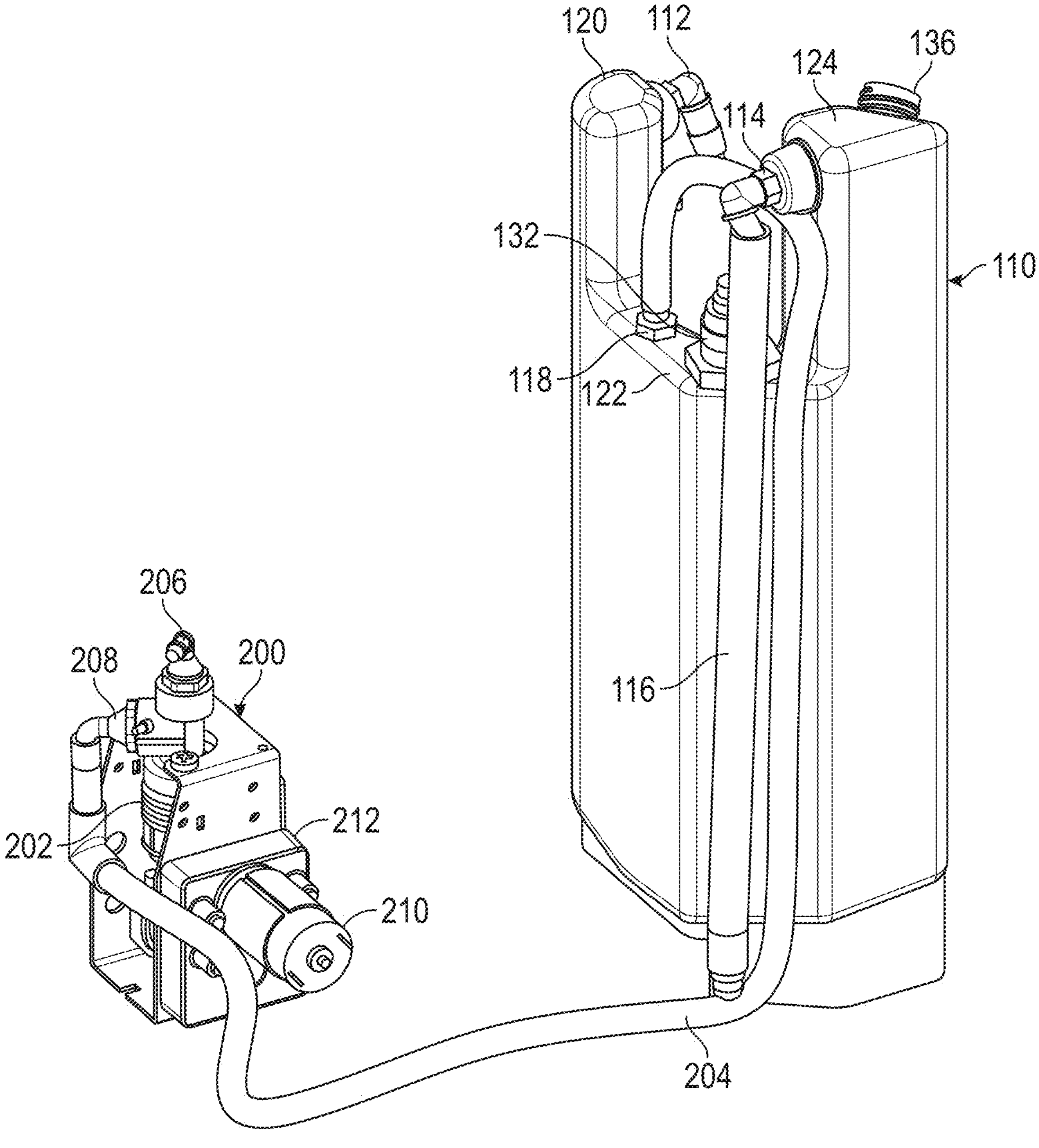
FIG. 5 is a front perspective view of the vacuum reservoir fluidly connected to a liquid transfer pump of the liquid waste management system.
Figure 5A:
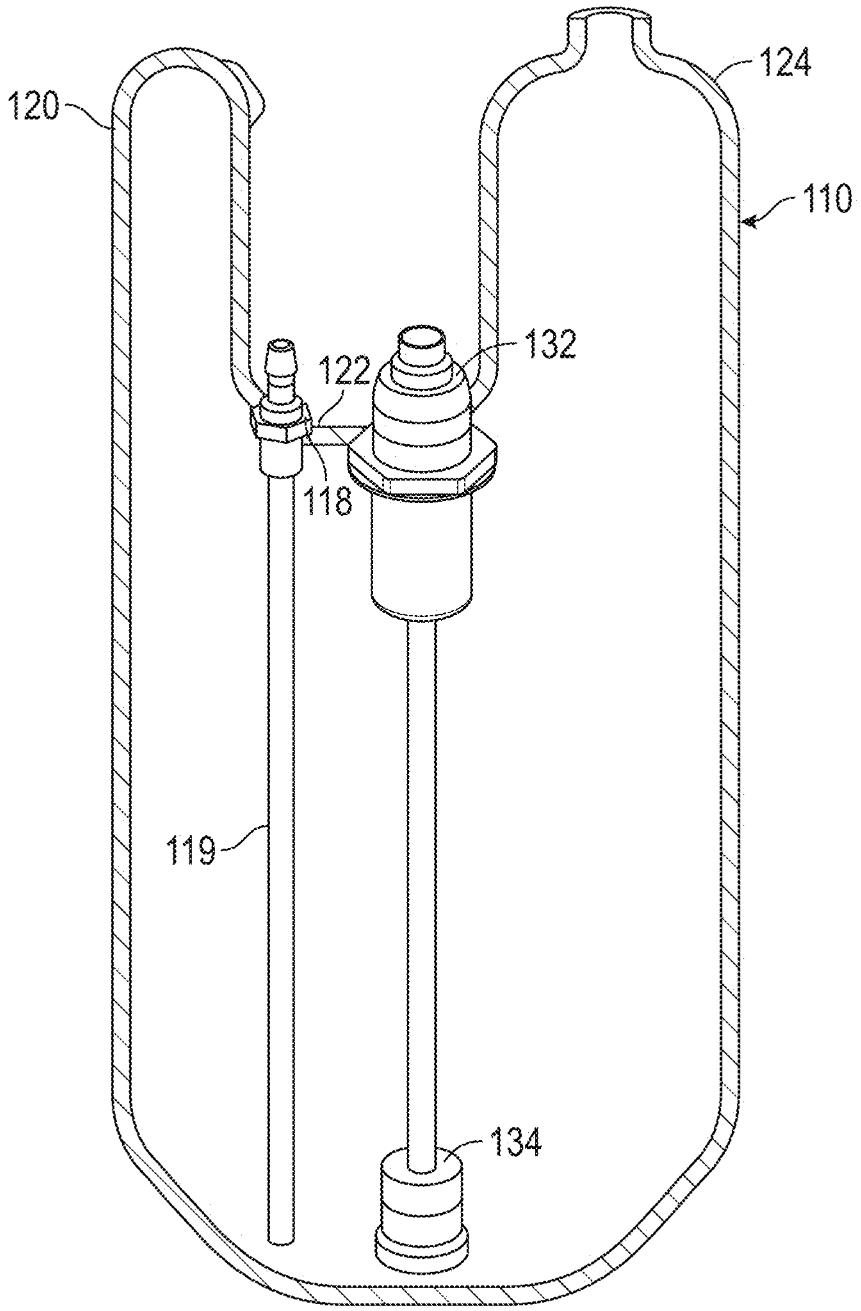
FIG. 5A is a transverse front cross-section of the vacuum reservoir.
Figure 6:
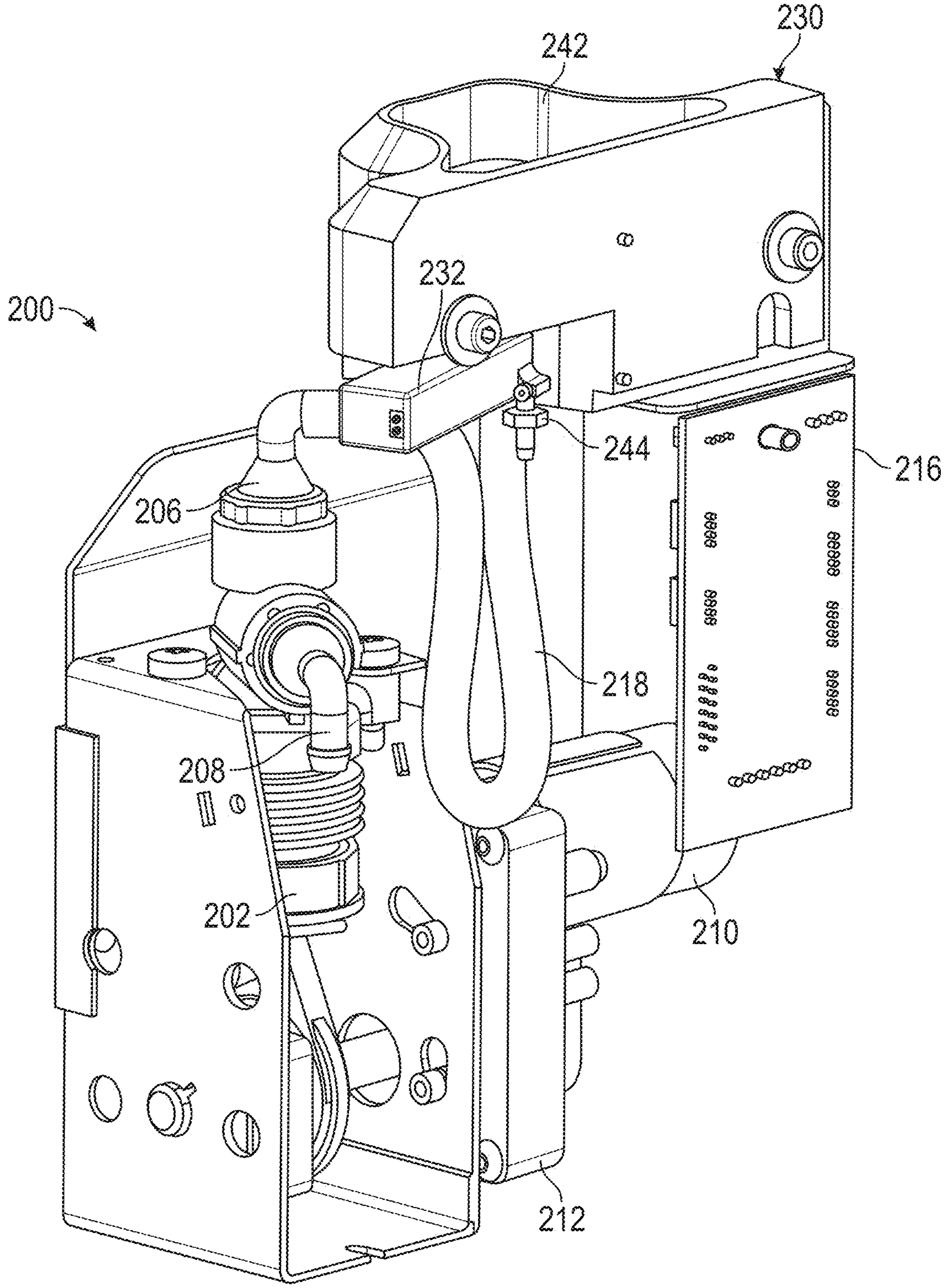
FIG. 6 is a perspective view of a transfer pump module of the liquid waste management system.
Figure 7:
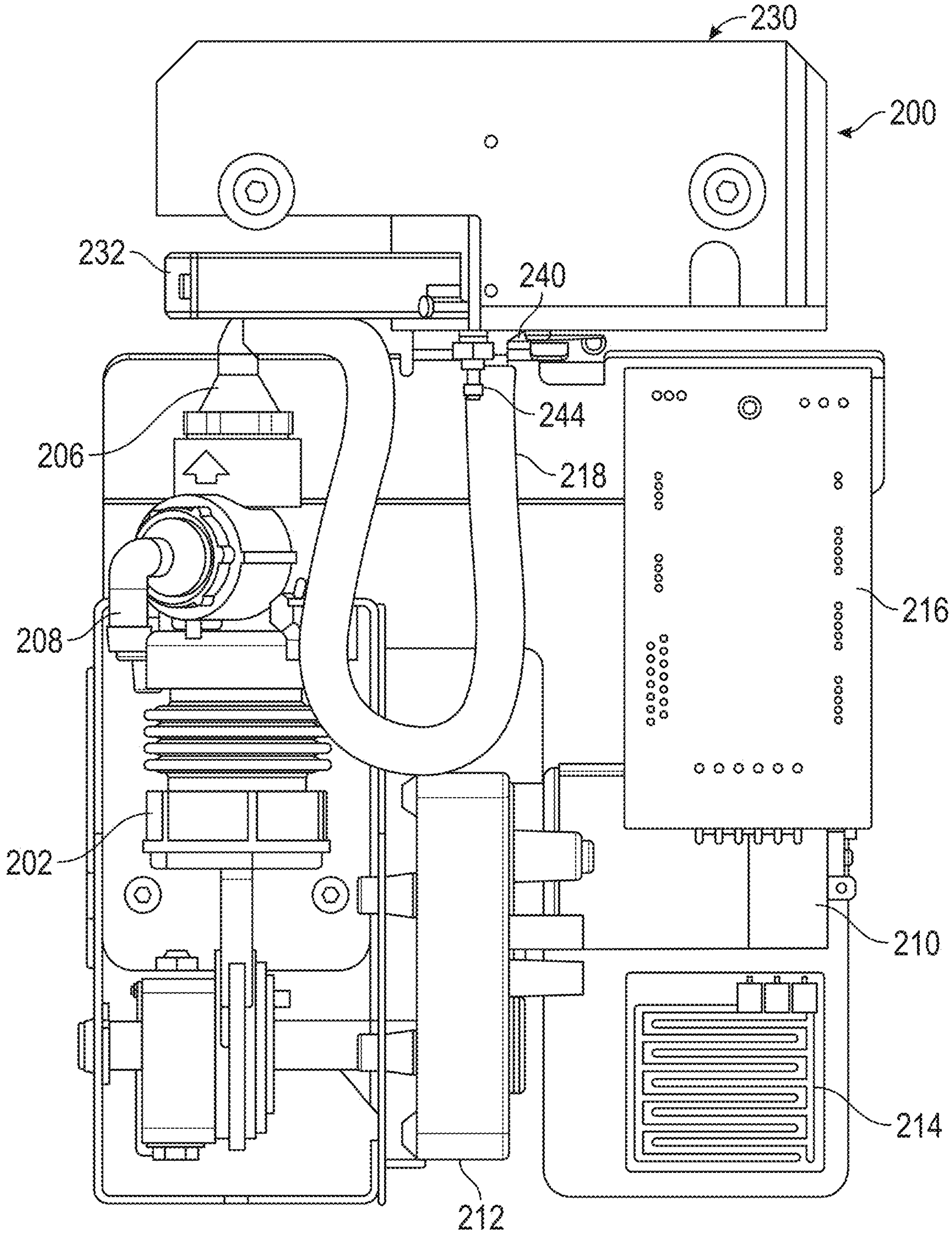
FIG. 7 is a side view of the transfer pump module.

As shown in FIG. 5, the transfer pump module 200 is connected to vacuum reservoir 110 by transfer line 204 (e.g., PVC tubing). Referring to FIGS. 5, 6, and 7, transfer pump module 200 includes a transfer pump 202, which may comprise a bellows pump (e.g., available from GRI Pumps, Bellville, OH), powered by a pump motor 210 with a pump transmission 212 coupling output of the pump motor 210 to the transfer pump 202. The transfer pump 202 includes a pump inlet port 208 and a pump outlet port 206. Liquid transfer line 204 is connected to transfer pump 202 at pump inlet port 208 and is connected to vacuum reservoir 110 at a transfer fitting 118 mounted in the intermediate top wall 122. In various embodiments, a tube (or straw) 119 (See FIG. 5A) extends into vacuum reservoir 110 below the intermediate top wall 122 from the transfer fitting 118. Tube, or straw, 119 may be formed from PVC. A pump outlet line 218 is connected at one end thereof to the pump outlet port 206.

The transfer pump module 200 may further include a leak detection sensor 214. Leak detection sensor 214 may comprise a foil with a serpentine conductor made from silicon and stainless steel that short circuits when exposed to liquid. A printed circuit board 216 may be provided with power and logic elements for controlling the liquid waste management system 100.

Referring to FIGS. 6 and 7, the transfer pump module 200 further includes a transfer container interface 230 releasably connecting transfer container 140 to transfer pump 202. As shown in FIGS. 6 and 7, transfer container interface 230 is mounted above the transfer pump 202. In an embodiment, transfer container interface 230 is affixed to the drawer 302. Pump outlet line 218 is connected to interface 230 at fitting 240 (see also FIGS. 10A, 10B).

Figure 9:
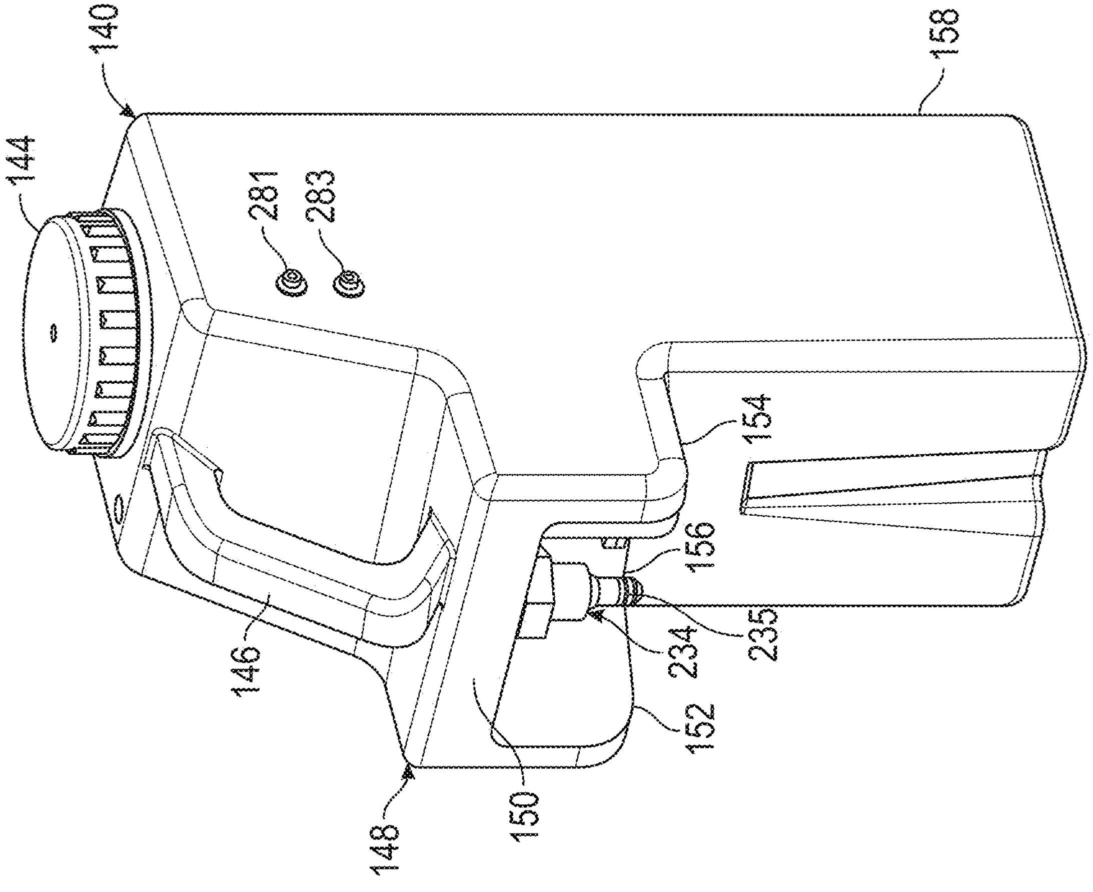
FIG. 9 is a top perspective view of a removable transfer container of the liquid waste management system.
Figure 11:
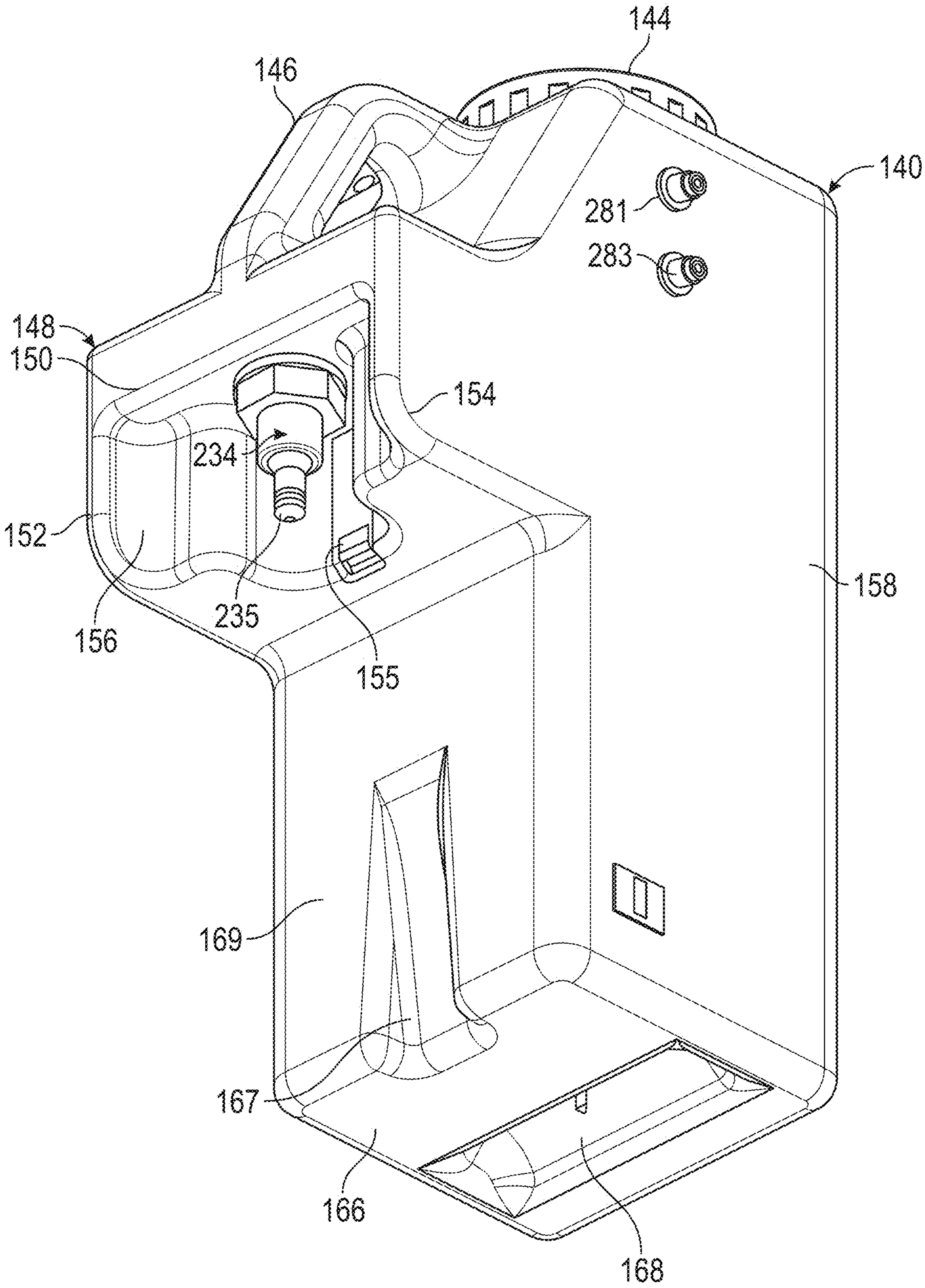
FIG. 11 is a bottom perspective view of the transfer container.

As shown in FIGS. 9 and 11, transfer container 140 includes a main body 158 with a cap 144 that can be removed from an opening of the container for emptying the transfer container 140. Transfer container 140 may further include a handle 146. Transfer container 140 can be manually emptied by lifting transfer container 140 with handle 146 out of the shelf or drawer (e.g., drawer 302) on which the liquid waste management system 100 is supported, and the cap 144 can be removed to permit the transfer container 140 to be emptied. As noted, drain line 184 may be optionally connected to transfer container 140 at a fitting 142 on top of the transfer container 140 (see FIG. 1) with a straw (not shown) extending from the fitting 142 into the interior of the transfer container 140.

Figure 10:
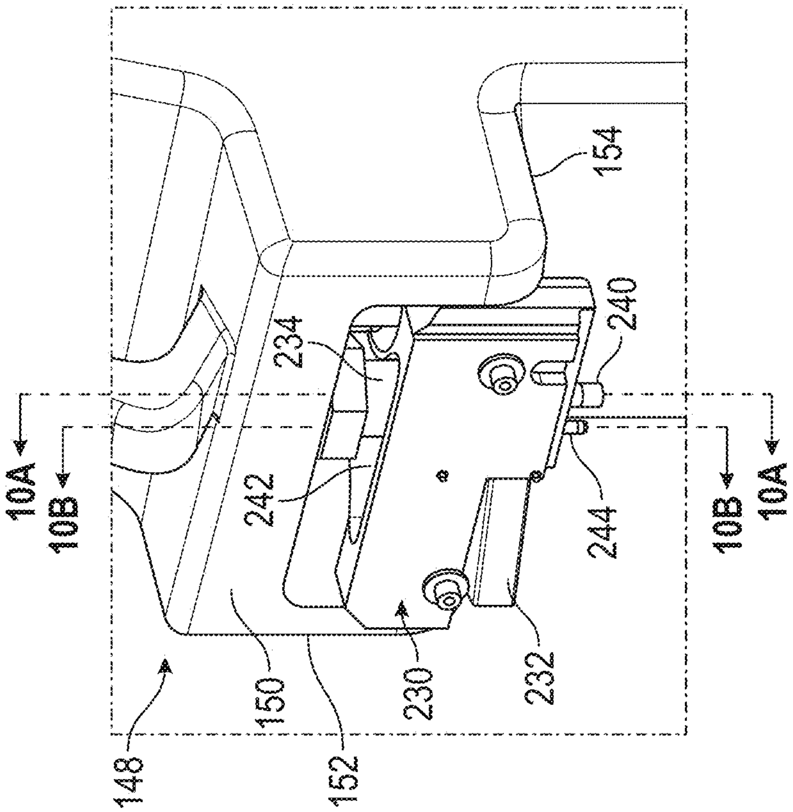
FIG. 10 is a partial perspective view of a portion of the transfer container.
Figure 10A:
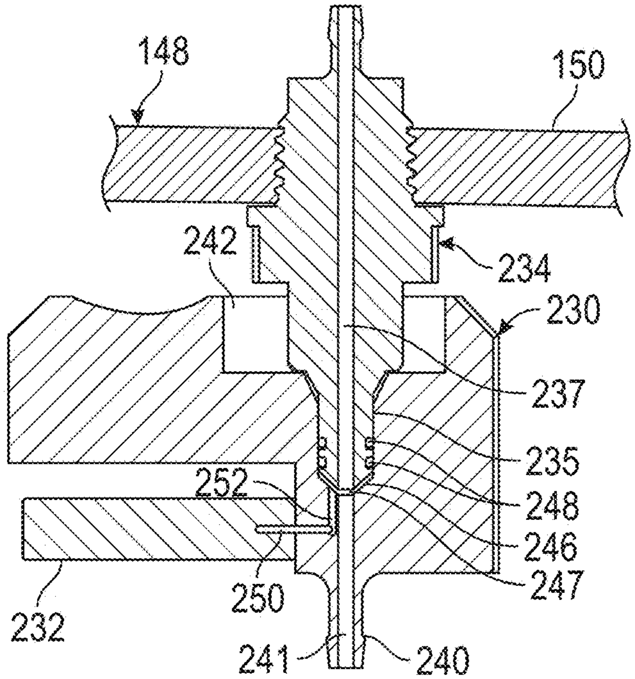
FIG. 10A is a side cross-sectional view of a liquid transfer connection between the transfer container and the removable container interface in the direction A-A in FIG. 10.
Figure 10B:
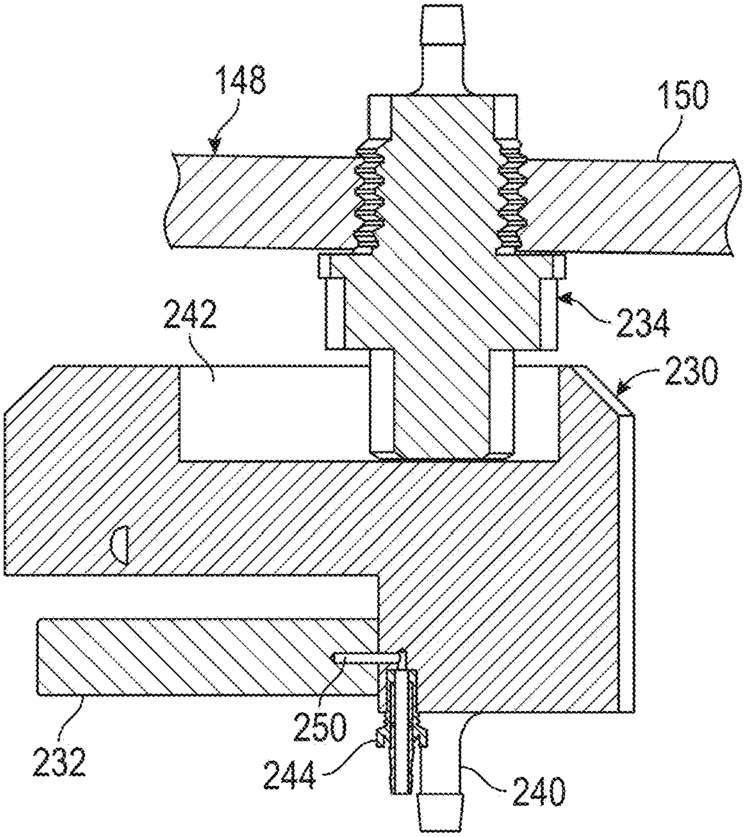
FIG. 10B is a side cross-sectional view of the liquid transfer connection between the transfer container and the removable container interface in the direction B-B in FIG. 10.

Transfer container 140 may further include a connector shelf 148 extending laterally from main body 158. Connector shelf 148 includes a horizontal portion 150, sidewalls 152, 154, and a male transfer inlet fitting 234 extending downwardly from a bottom wall of horizontal portion 150. Sidewalls 152, 154 and the horizontal portion 150 define an open recess 156 that, as shown in FIG. 10, receives transfer container interface 230. As shown in FIGS. 10, 10A, 10B, the male transfer inlet fitting 234 extends into a conforming female receptor 246 disposed within a liquid trough 242 formed in the top of removable container interface 230, thereby fluidly connecting transfer container 140 to the liquid transfer pump 202. Thus, liquid transfer pump 202 can pump liquid from vacuum reservoir 110 via the transfer line 204 and into transfer container 140.

As shown in FIG. 11, transfer container 140 may further include a recess 168 formed in a bottom surface 166 of body 158 and an angled slot 167 extending from the bottom surface 166 partially up a side wall 169 beneath the connector shelf 148. Recess 168 is a hand-hold location when the user is pouring liquid out of the transfer container 140. Slot 167 is a ramp for a mechanical presence sensor (not shown), which has a retractable rod that, when depressed, indicates the presence of transfer container 140. Ramp 168 aided in seating the bottle into the drawer properly and gradually depressing the mechanical switch.

As an alternative to a mechanical switch, a reed switch with a magnet for a presence sensor. Referring to FIG. 11, a magnet 155 may be mounted within an exterior surface of the transfer container 140 surrounding open recess 156. In an embodiment, a magnetic proximity sensor, such as sensor 243 mounted in transfer container interface 230 (see FIG. 8), detects the magnet 155 when the transfer container 140 is in its operative position with respect to the transfer container interface 230 and pump module 200 (as shown in FIG. 1).

Figure 12A:
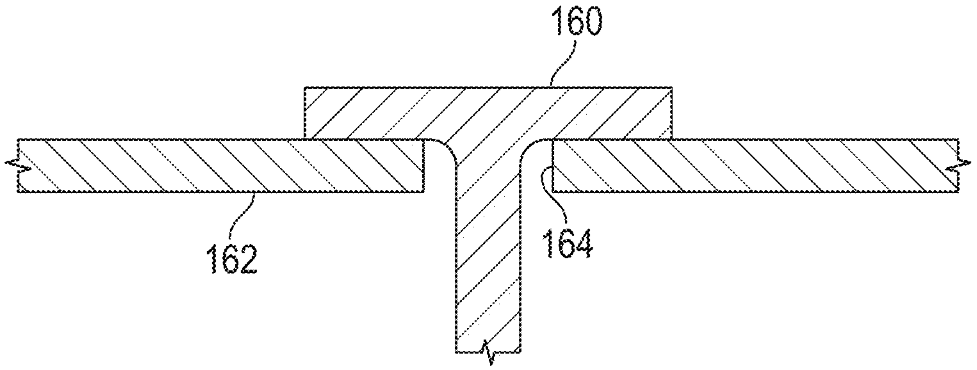
FIG. 12A is a side perspective view of a poppet valve within the transfer container shown in a closed position.
Figure 12B:
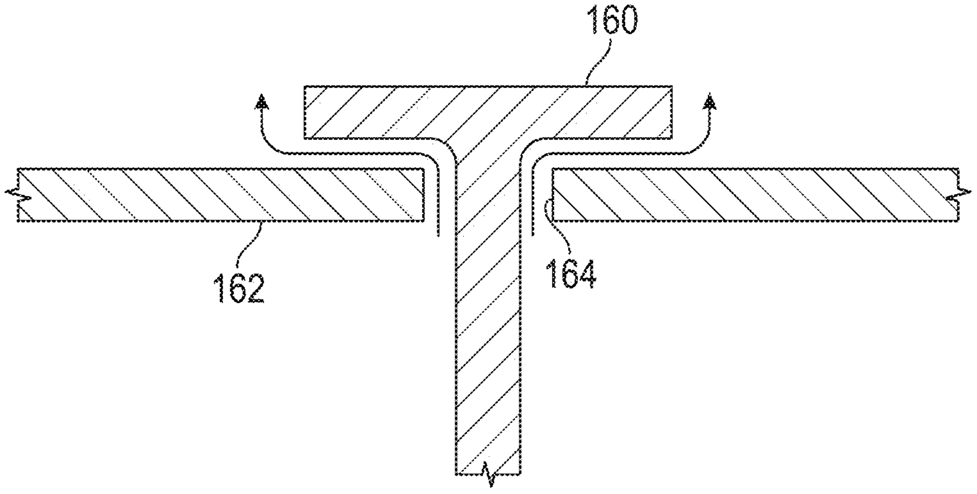
FIG. 12B is a side perspective view of a poppet valve within the transfer container shown in an open position.

Referring to FIGS. 12A and 12B, transfer container 140 may include a poppet valve 160 disposed within an intake port 164 of a container wall 162 within the horizontal portion 150 of connector shelf 148 or disposed within the transfer inlet fitting 234. Poppet valve 160 is configured to move from a closed position shown in FIG. 12A, when the transfer pump 202 is not pumping liquid from vacuum reservoir 110, to an open position shown in FIG. 12B, when the transfer pump 202 is pumping liquid. Thus, a pressure differential caused by the transfer pump 202 opens the poppet valve 160 to permit liquid to be pumped into transfer container 140, and the poppet valve 160 closes in the absence of a pressure differential to prevent liquid from escaping the transfer container 140.

Transfer container 140 may further include a liquid level sensor for detecting a liquid level within the container 140 and provide a signal indicating that the container should be emptied or should be emptied soon. An exemplary liquid level sensor that may be incorporated into the transfer container 140 is indicated by reference number 266 in FIGS. 16, 17, 18. Liquid level sensor 266 includes a sensor bracket 280, which may be secured to a wall of the transfer container 140 by screws or rivets 281 and 283. Liquid level sensor 266 further includes a lower float 282 and an upper float 288. Lower float 282 is pivotably mounted to the sensor bracket 280 by a pin 286 and includes a magnet 284 mounted within a face of the float 282. Similarly, upper float 288 is pivotably mounted to the sensor bracket 280 by a pin 292 and includes a magnet 290 mounted within a face of the float 288.

Figure 16:
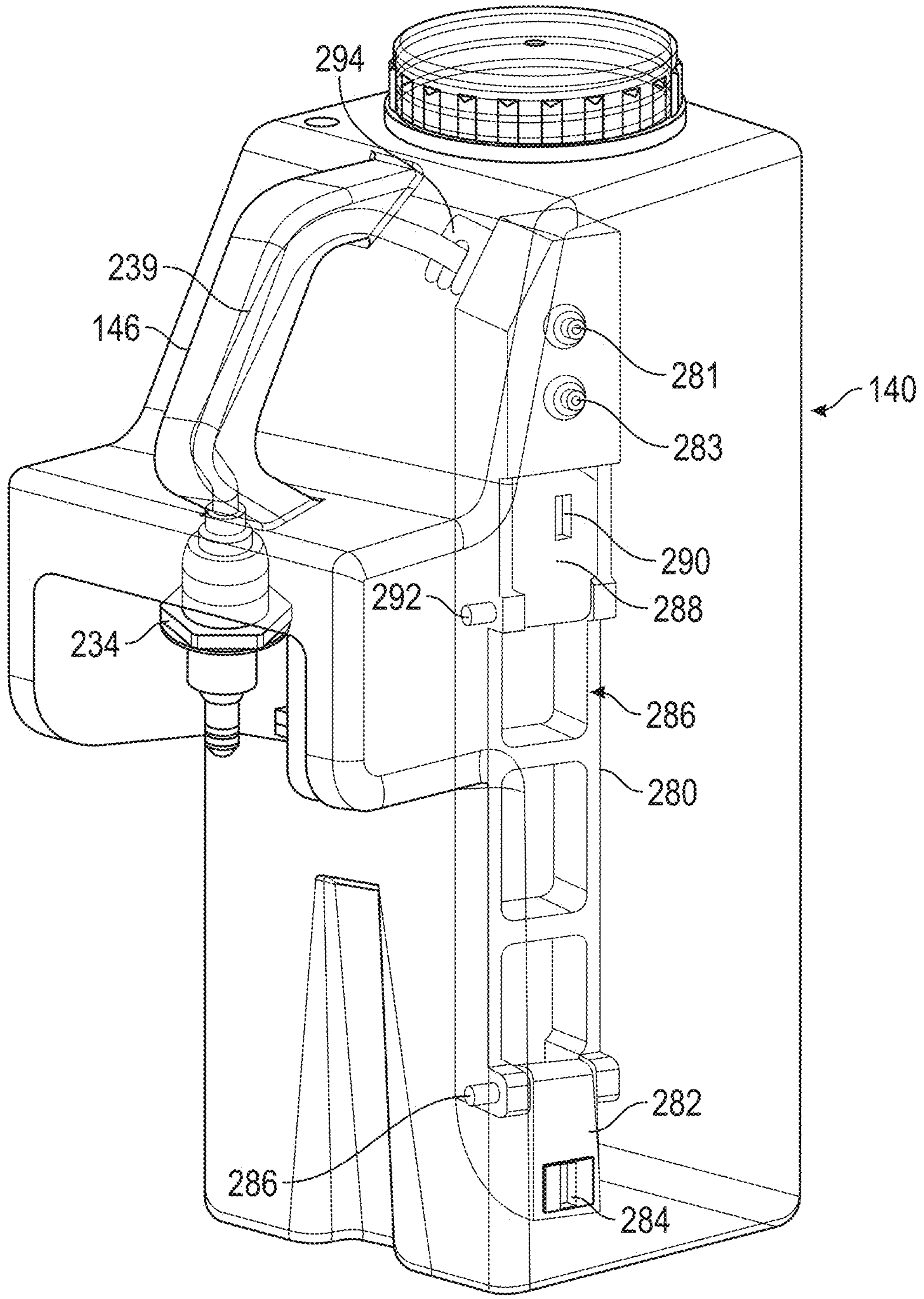
FIG. 16 is a perspective view of the transfer container showing a liquid level sensor located within the interior of the container.
Figure 17:
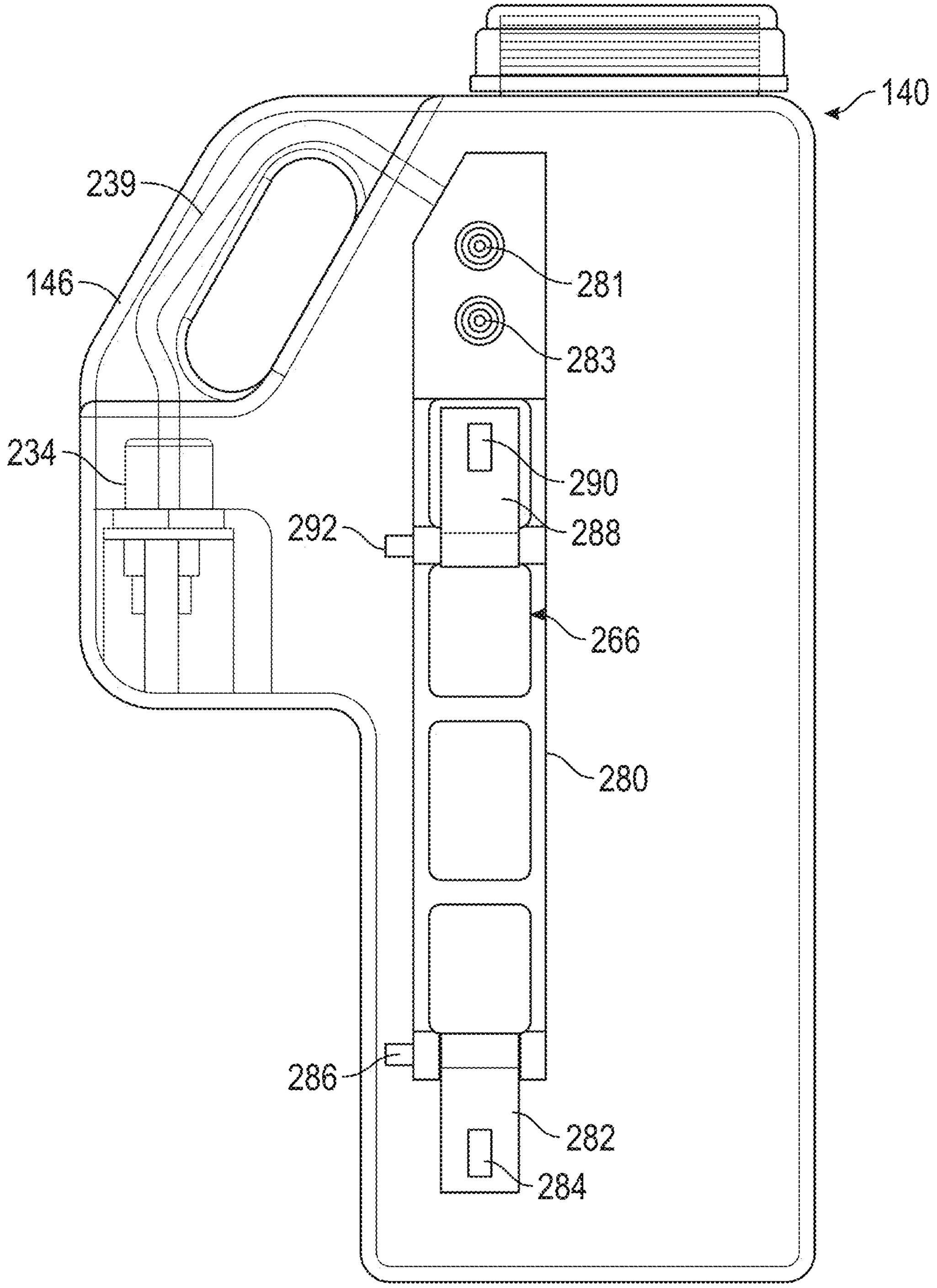
FIG. 17 is a side view of the transfer container showing a liquid level sensor located within the interior of the container.
Figure 18:
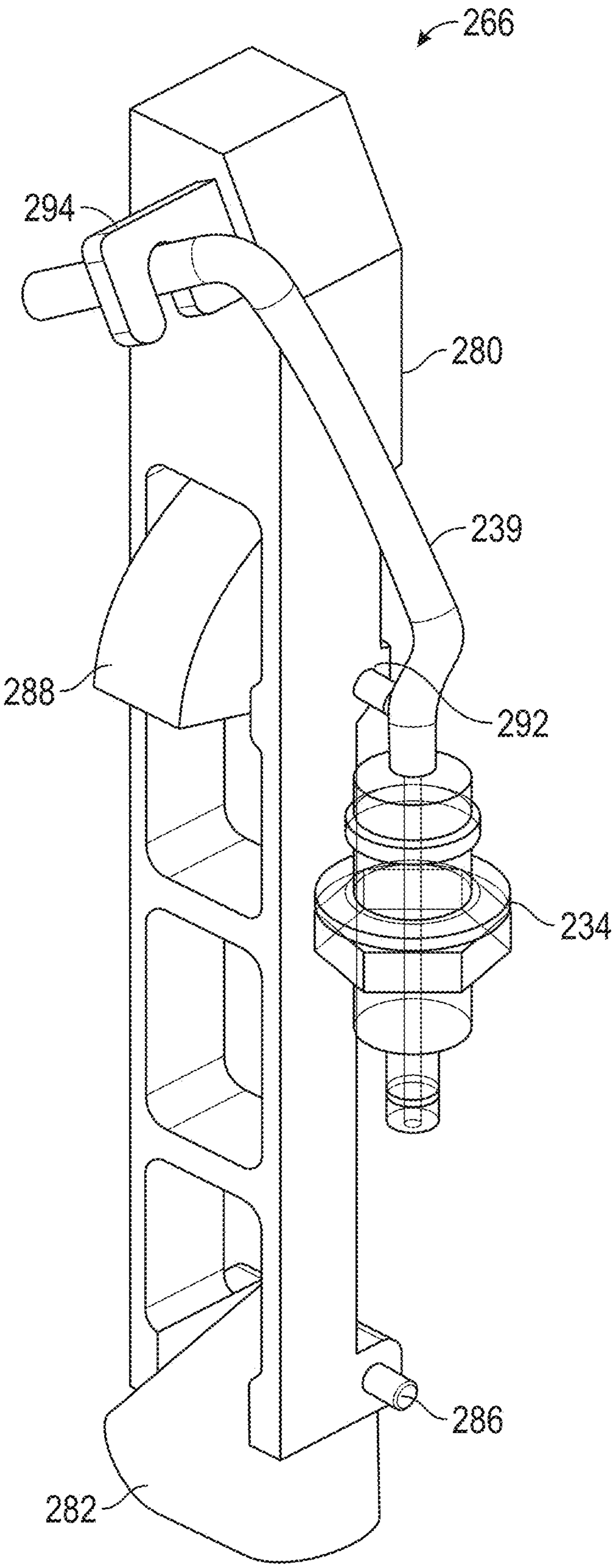
FIG. 18 is a perspective view of the liquid level sensor.

When there is little or no liquid within the transfer container 140, the lower float 282 will hang in a downward position as shown in FIGS. 16-18, thereby presenting the magnet 284 in an outwardly facing orientation toward a wall of the transfer container 140. The outwardly facing magnet 284 will be detected by a lower magnetic proximity sensor 304 mounted in a front wall of the drawer 302, as shown in FIG. 15. Thus, a positive signal from the lower proximity sensor 304 indicating detection of the magnet 284 will indicate that the transfer container 140 is empty or nearly empty. As liquid begins to fill the transfer container 140, buoyancy of the float 282 will cause the float 282 to rotate about the pin 286, thereby moving the magnet 284 from the outwardly facing orientation. Thus, the magnet will no longer be detected by the lower proximity sensor 304, thereby indicating that liquid is being transferred into the transfer container 140.

When the liquid level within the transfer container 140 reaches the upper float 288, buoyancy of the float 288 will cause the float 288 to rotate upwardly about the pin 292 to the position shown in FIGS. 16-18, thereby presenting the magnet 290 in an outwardly facing orientation toward a wall of the transfer container 140. The outwardly facing magnet 290 will be detected by an upper magnetic proximity sensor 306 mounted in a front wall of the drawer 302, as shown in FIG. 15. Thus, a positive signal from the upper magnetic proximity sensor 306 indicating detection of the magnet 290 will indicate that the liquid within transfer container 140 is at or near a level at which the transfer container 140 should be emptied. An alarm (e.g., visual and/or audible) may signal an operator to empty the container 140. Alternatively, a positive signal from upper magnetic proximity sensor 306 may activate a drain pump (described below) to remove liquid from the container 140.

Until the liquid within transfer container 140 reaches the upper float 288, the float 288 will hang downwardly, thereby positioning the magnet 290 away from the outwardly facing orientation. Thus, the magnet will not be detected by the upper proximity sensor 306.

Figure 8:
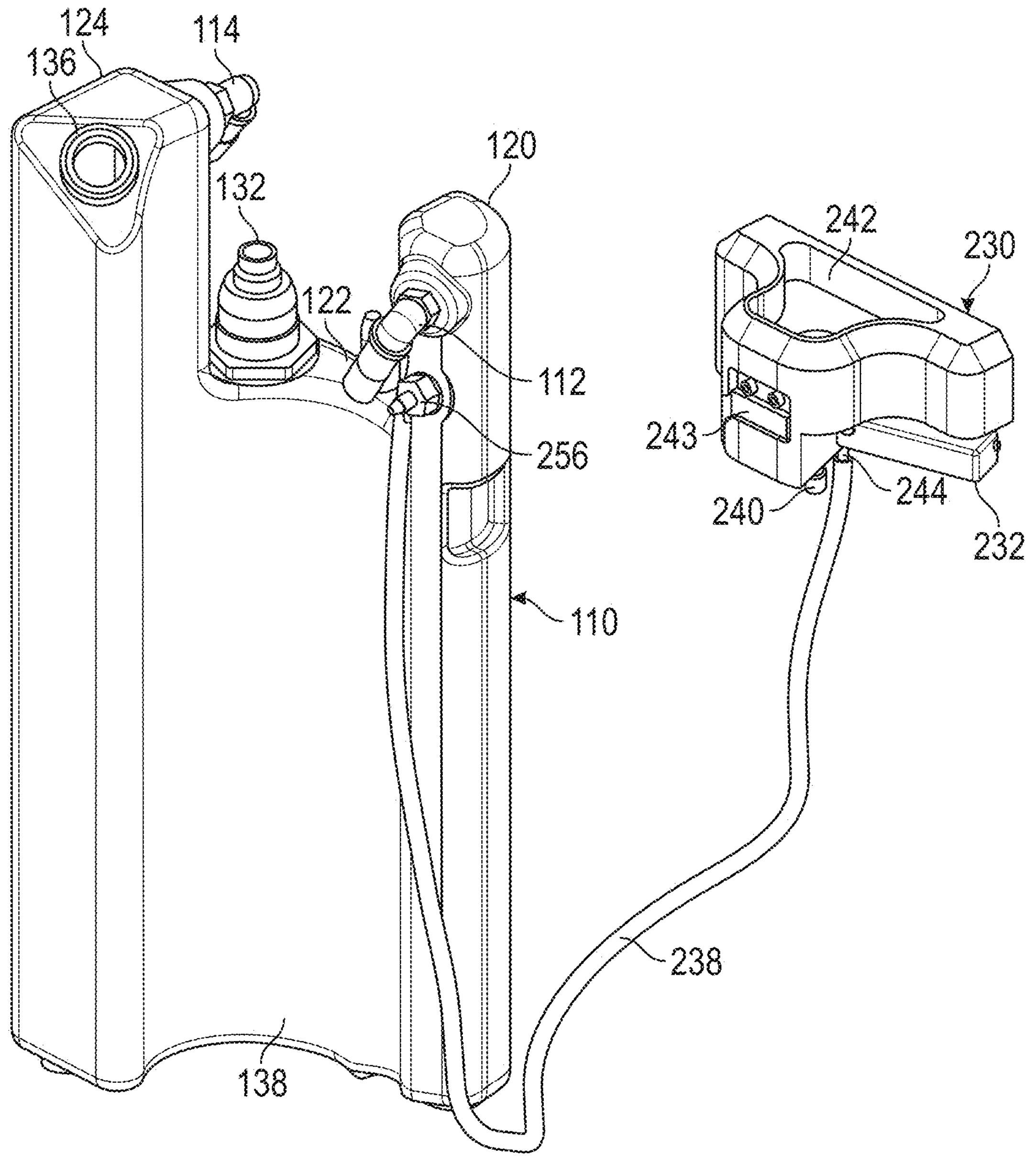
FIG. 8 is a rear perspective view of the vacuum reservoir and a removable container interface of the liquid waste management system with the filter and a filter mounting block omitted from the figure.

FIGS. 10A and 10B show features of a connection between transfer container 140 and transfer container interface 230. Male transfer inlet fitting 234 (also referred to herein as liquid transfer connector fitting) includes a nipple 235 that extends downwardly from horizontal portion 150 of the connector shelf 148 into the female receptor opening 246 formed in the container interface 230 and a liquid channel 237 extending through the fitting 234. One or more O-rings 248 may be provided between an exterior surface of nipple 235 and an interior surface of the female receptor opening 246. O-rings 248 are preferably formed from a bleach compatible material, such as EPDM or Viton®. A flow channel 241 extends from the bottom of the receptor opening 246 through the fitting 240. As shown in FIGS. 16-18, a tube 239 extends from the transfer inlet fitting 234 into the interior of the transfer container 140 and may extend through the handle 146 to a clip 294 on the sensor bracket 280. Drip channels 250, 252 extend from the bottom of the receptor opening 246 to a drip control valve 232 connected to a drip line connector fitting 244. Drip line connector fitting 244 may comprise a right angle, barbed fitting with NPT (National Pipe Taper) threads and is preferably formed from a bleach compatible material, such as PP, PVDF, etc. Referring to FIG. 8, a drip line 238 (e.g., PVC tubing) is connected to drip line connector fitting 244 of transfer container interface 230 and extends to a drip line fitting 256 disposed in the liquid inlet tower 120 of vacuum reservoir 110. Drip line fitting 256 may comprise a right angle, barbed fitting with NPT (National Pipe Taper) threads and is preferably formed from a bleach compatible material, such as PP, PVDF, etc. Drip control valve 232, which may be a solenoid valve, controls flow through drip line 238. Drip control valve 232 opens while and/or after liquid is pumped by transfer pump 202 into transfer container 140. In an embodiment, drip control valve 232 is configured and controlled to be in the open configuration after the liquid transfer pump 202 has been deactivated and before the transfer container 140 is removed from system 100 for liquid waste disposal. In an embodiment, drip control valve 232 is only open for a prescribed period of time (e.g., a few seconds (2-10 seconds)) and draws liquid from (i) the interface between exterior surface of nipple 235 and interior surface of the female receptor opening 246 (for example, from a gap 247 between nipple 235 and female receptor opening 246 (see FIG. 10A)), and (ii) the liquid channel 237 extending through male transfer inlet fitting 234. In another embodiment, drawer 302 is locked during operation of the instrument and can be unlocked, for example using a touch screen (e.g., a waste management screen) of an instrument control computer. When an operator has requested that the drawer 302 be unlocked, but before the instrument unlocks the drawer 302, drip control valve 232 may open for a brief period, e.g., 2-10 seconds, to remove liquid from male transfer inlet fitting 234 before the transfer bottle 140 is removed from the drawer 302. Drip line 238, connected to drip control valve 232, connects to vacuum reservoir 110 under vacuum. When drip control valve 232 is open, any remaining liquid on the surface of or inside female receptor opening 246 or liquid trough 242 is pulled under vacuum back into vacuum reservoir 110 through drip line 238.

Operation of the liquid waste management system 100 and the interrelationship of various components are illustrated in FIG. 13. Vacuum reservoir 110 is connected to a pressure differential source, such as a vacuum pump 274, that draws air from the vacuum tower 124 of vacuum reservoir 110 through the vacuum filter loop 116, filter 128, and vacuum line 180. Liquid waste is drawn from a liquid waste source, such as one or more aspirators 276, through liquid waste inlet line 182 into liquid inlet tower 120 of vacuum reservoir 110.

Liquid level within vacuum reservoir 110 is monitored via float switch 134, which is in direct or indirect (e.g., through a system controller), wired or wireless, communication with transfer pump 202, as represented by a transfer pump signal communication path 270. When liquid within vacuum reservoir 110 reaches a predefined level, as determined by float switch 134, an activation signal is transmitted to the transfer pump 202. In an embodiment, float switch 134 communicates liquid level height within the vacuum reservoir 110 as a fraction or percentage of a maximum height. When the height percentage exceeds a threshold defined by software that controls operation of the liquid waste management system 100, a command is sent to the transfer pump 202 to turn on.

Other means may be used to monitor the amount of liquid in the vacuum reservoir 110, such as a scale (not shown) measuring the weight of the vacuum reservoir 110 and its contents or a contact switch (not shown) mounted to an interior surface of the vacuum reservoir 110 that is activated when contacted by liquid within the vacuum reservoir 110.

Transfer pump 202 is then activated to transfer liquid from vacuum reservoir 110 via the liquid transfer line 204 and the pump outlet line 218 to transfer container 140 that is connected to the pump outlet line 218 via the transfer inlet fitting 234 disposed on the horizontal portion 150 of connector shelf 148. Transfer pump 202 may be activated for a prescribed period of time, until all liquid is removed from the vacuum reservoir 110 (i.e., when the liquid height percentage drops to 0%), as determined by float switch 134, scale, or interior contact switch, or until a prescribed amount of liquid is removed from the vacuum reservoir 110, as determined by float switch 134, scale, or interior contact switch or by a flow meter (not shown).

Drip control valve 232 is in direct or indirect, wired or wireless, communication with transfer pump 202, as represented by drip valve signal communication path 272, so that as the transfer pump 202 is pumping liquid into transfer container 140 (and/or shortly thereafter), valve 232 is opened, thereby drawing liquid under vacuum through the drip line 238 from the transfer inlet fitting 234, female receptor 246, and/or liquid trough 242 and into the vacuum reservoir 110.

Transfer container 140 can be manually emptied, as described above. Alternatively, drain pump 262 (e.g., a bellows pump available from GRI Pumps, Bellville, OH), may be provided connecting transfer container 140 to a drain 260 via drain line 184. Liquid level within transfer container 140 may be monitored via liquid level sensor 266 within transfer container 140. Liquid level sensor 266 may be in direct or indirect (e.g., through a system controller) communication, wired or wireless, with drain pump 262, as represented by a drain pump signal communication path 268. When liquid within transfer container 140 reaches a predefined level, as determined by liquid level sensor 266, an activation signal is transmitted to the drain pump 262. Other means may be used to monitor the amount of liquid in the transfer container 140, such as a scale (not shown) measuring the weight of the transfer container 140 and its contents or a contact switch (not shown) mounted to an interior surface of the transfer container 140 that is activated when contacted by liquid within the transfer container 140.

Drain pump 262 is then activated to draw liquid from transfer container 140 to drain 260 via drain line 184. Drain pump 262 may be activated for a prescribed period of time, until all liquid is removed from the transfer container 140, as determined by liquid level sensor 266, scale, or interior contact switch, or until a prescribed amount of liquid is removed from the transfer container 140, as determined by liquid level sensor 266, scale, or interior contact switch or by a flow meter (not shown).

Liquid waste management system 100 may include an indicator, such as, an alarm, warning light, audio and/or visual message generator, or the like, coupled to the liquid level sensor 266 to indicate that the amount of liquid in the transfer container 140 has reached or exceeded a predefined threshold. In certain embodiments, the instrument ceases processing samples once a predefined threshold has been reached. An advance warning may be provided to avoid having to stop the processing of samples.

Control System

Liquid waste management system 100 may include a controller 500, which monitors, communicates with, and/or controls components of system 100, including one or more of the transfer pump 202, the drip control valve 232, float switch 134, liquid level sensor 266 (which includes proximity sensors 304, 306), drain pump 262, proximity sensors 243, and vacuum pump 274. Controller 500 may be in wired or wireless communication with each of the components monitored and/or controlled by controller 500. To avoid obscuring the drawing, communication lines between controller 500 and components of the system 100 are not shown in FIG. 13.

Controller 500 may comprise a computer system for executing software (which may include firmware) that effects operation, control, and monitoring of the liquid waste management system 100. Controller 500 may be implemented via one or more logic elements, e.g., a computer, embedded controller, programmable gate array, application specific integrated circuit, programmable logic device, etc., and may include or access data storage memory, which may include random access memory (RAM), read only memory (ROM), flash memory, and other types of memory now known or later developed. Controller 500 may also include additional memory, including, for example, a hard disk drive and/or a removable storage drive, representing a magnetic tape drive, an optical disk drive, USB slot, memory card interface, internet memory, cloud-based memory, or any storage medium or format now known or later developed. Memory devices and storage units used herein may comprise any storage medium for persistent and/or volatile storage of electronic data now known or later developed. Such data may be stored within the storage medium in a database, which may comprise any data structure and format now known or later developed, including, for example, a relational database, an object database, a flat file, list, and so on, or some combination thereof.

In alternative embodiments, some or all of the memory may include other similar means for allowing computer programs or other instructions to be loaded into a computer system. Such means can include, for example, a removable storage unit and an interface. Examples of such can include a memory stick and memory stick interface, a secure digital card and interface, and other portable media and interfaces which allow software and data to be transferred to controller 500.

Software comprises instructions stored on non-transitory computer-readable media which, when executed by the logic element(s) of the controller 500, cause the control and computing hardware to perform one or more automated or semi-automated processes.

The computer system of controller 500 may also include a communications interface, which allows information (e.g., power, control and feedback signals, software, data, etc.) to be transferred between controller 500 and external devices. Examples of communications interfaces can include a modem, a network interface (such as an Ethernet card), a communications port, a PCMCIA slot and card, a USB-port, a Firewire port, Bluetooth, or any interface now known or later developed. Information transferred via a communications interface is in the form of signals which can be electronic, electromagnetic, optical or other signals capable of being received by the communications interface.

The computer system of controller 500 can also include one or more input devices, such as a touch screen, stylus, keyboard, mouse or other pointing device, microphone (voice recognition), data scanners (e.g., barcode, RFID, etc.), and so on. Various output devices may also be included in the computer system, including indicator lights, a display, printer, tactile (e.g., vibratory) indicators, and audio speakers.

In this document, terms such as "computer program medium," "computer-readable medium." "computer usable medium," and the like are used to generally refer to media, such as removable storage units, a hard disk installed in hard disk drive, and other non-transitory means for providing software and data to controller 500.

Computer programs (also called computer control logic) are stored in one or more portions of memory that is part of or accessed by controller 500. Computer programs can also be received via a communications interface. Such computer programs may include algorithms that, when executed, enable the computer system of controller 500 to control the operation of the liquid waste management system 100 in accordance with aspects disclosed herein.

In an embodiment in which aspects of the subject matter disclosed herein are implemented using software, the software may be stored in a computer program product and loaded into the computer system of controller 500 using a removable storage drive, a hard drive, an interface, and/or a communications interface. The control logic (software), when executed by the processor of the controller 500, causes the processor to perform functional aspects of the subject matter as described herein via the systems, devices, apparatuses, sensors, encoder, etc. described above. An operating system may perform basic tasks such as recognizing input from an input device, sending output to an output device, managing files and system resources, and managing the various processes embodying computer programs running on the computer system.

Controller 500 may comprise a stand-alone system dedicated to the liquid waste management system 100, or one or more components of controller 500—e.g., processor, memory, interfaces, input/output devices, etc.—may be a shared part of a global controller that controls one or more components of an instrument or laboratory of which the liquid waste management system 100 is a component, in addition to the liquid waste management system 100.

EMBODIMENTS

Embodiment 1. A system for managing liquid waste, the system comprising: a first liquid container configured to receive liquid from a liquid source; a liquid transfer pump fluidly connected to the first liquid container; and a second liquid container fluidly connectable to the liquid transfer pump, wherein the liquid transfer pump is configured to be selectively activated to transfer liquid from the first liquid container to the second liquid container when the second liquid container is fluidly connected to the liquid transfer pump.

Embodiment 2. The system of embodiment 1, further comprising a pressure differential source to which the first liquid container is connected to draw liquid into the first liquid container from the liquid source.

Embodiment 3. The system of embodiment 2, wherein the pressure differential source comprises a vacuum pump.

Embodiment 4. The system of embodiment 3, further comprising a filter between the vacuum pump and the first liquid container.

Embodiment 5. The system of embodiment 4, wherein the filter comprises a bleach fume filter.

Embodiment 6. The system of embodiment 4 or 5, further comprising a mounting block on which the filter and the first liquid container are mounted.

Embodiment 7. The system of embodiment 6, further comprising a filter loop fluidly connecting a top portion of the first liquid container to a bottom portion of the filter supported on the mounting block.

Embodiment 8. The system of any one of embodiments 3 to 7, wherein the first liquid container comprises: an intermediate top wall; a first tower extending above the intermediate top wall; and a second tower extending above the intermediate top wall; wherein the first tower includes a liquid inlet in the first tower for receiving liquid from the liquid source into the first liquid container, and wherein the second tower includes a vacuum fitting in the second tower to which the vacuum pump is attached to draw liquid into the first liquid container from the liquid source.

Embodiment 9. The system of any one of embodiments 1 to 8, wherein the liquid transfer pump comprises a bellows pump.

Embodiment 10. The system of any one of embodiments 1 to 9, further comprising a motor for operating the liquid transfer pump and a transmission coupling the motor to the liquid transfer pump.

Embodiment 11. The system of any one of embodiments 1 to 10, further comprising a poppet valve associated with the second liquid container for controlling liquid flow into the second liquid container.

Embodiment 12. The system of any one of embodiments 1 to 11, further comprising a float switch within the first liquid container, wherein the float switch is in communication with the liquid transfer pump to activate the liquid transfer pump when liquid within the first liquid container reaches a predefined level.

Embodiment 13. The system of any one of embodiments 1 to 12, further comprising a connector fitting for fluidly connecting the second liquid container to the liquid transfer pump and a drip management system configured to draw liquid from the connector fitting into the first liquid container.

Embodiment 14. The system of embodiment 1, further comprising: a connector fitting for fluidly connecting the second liquid container to the liquid transfer pump; a drip management system configured to draw liquid from the connector fitting into the first liquid container; and a vacuum pump to which the first liquid container is connected to draw liquid into the first liquid container from the liquid source, and wherein the connector fitting comprises a female connector member and a male connector member received within the female connector member, and wherein the drip management system comprises a connection port in communication with the female connector member, a fluid conduit connecting the connection port to the first liquid container, and a drip control valve, wherein the drip control valve is configured to permit fluid flow through the fluid conduit when the drip control valve is in an open configuration and to prevent fluid flow through the fluid conduit when the drip control valve is in a closed configuration.

Embodiment 15. The system of embodiment 14, wherein the drip control valve is a solenoid valve.

Embodiment 16. The system of embodiment 14 or 15, wherein the drip control valve is configured and controlled to be in the open configuration after the liquid transfer pump is deactivated following a transfer of liquid from the first liquid container to the second liquid container Embodiment 17. The system of embodiment 16, wherein the drip control valve is configured and controlled to be in the open configuration for a prescribed period of time after the liquid transfer pump is deactivated following the transfer of liquid from the first liquid container to the second liquid container and to be in the closed configuration all other times.

Embodiment 18. The system of any one of embodiments 1 to 12 wherein the second liquid container comprises: a main body; a connector shelf extending laterally from the main body and including a horizontal portion and defining a bottom wall; and a liquid transfer connector fitting extending downwardly from the bottom wall of the horizontal portion of the connector shelf for fluidly connecting the second liquid container to the liquid transfer pump.

Embodiment 19. The system of embodiment 18, further comprising a connector interface fluidly connected to the liquid transfer pump and including an upwardly facing liquid connector fitting configured to be operably coupled to the downwardly extending liquid transfer connector fitting of the second liquid container to fluidly connect the liquid transfer pump to the second liquid container.

Embodiment 20. The system of embodiment 19, further comprising a liquid tray formed in the connector interface and surrounding the upwardly facing liquid connector fitting of the connector interface.

Embodiment 21. The system of embodiment 20, further comprising a drip management system configured to draw liquid from the liquid tray to the first liquid container or from the operably coupled liquid transfer connector fittings of the connector interface and the second liquid container to the first liquid container.

Embodiment 22. The system of embodiment 21, wherein the drip management system comprises: a connection port attached to the connector interface; a fluid conduit connecting the connection port to the first liquid container; and a drip control valve, wherein the drip control valve is configured to permit fluid flow through the fluid conduit when the drip control valve is in an open configuration and to prevent fluid flow through the fluid conduit when the drip control valve is in a closed configuration.

Embodiment 23. The system of embodiment 22, wherein the drip control valve is a solenoid valve.

Embodiment 24. The system of embodiment 22 or 23, wherein the drip control valve is configured and controlled to be in the open configuration when the liquid transfer pump is deactivated following a transfer of liquid from the first liquid container to the second liquid container.

Embodiment 25. The system of embodiment 24, wherein the drip control valve is configured and controlled [to be] to be in the open configuration for a prescribed period of time after the liquid transfer pump is deactivated following the transfer of liquid from the first liquid container to the second liquid container and to be in the closed configuration all other times.

Embodiment 26. The system of any one of embodiments 1 to 21, further comprising: a drain line connected to the second liquid container; and a drain pump fluidly connected to the drain line for transferring liquid from the second liquid container to a drain via the drain line.

Embodiment 27. The system of embodiment 26, further comprising a second float switch within the second liquid container, wherein the second float switch is in communication with the drain pump to activate the drain pump when liquid within the second liquid container reaches a predefined level.

Embodiment 28. The system of any one of embodiments 1 to 27, further comprising a leak detection sensor.

Embodiment 29. The system of any one of embodiments 1 to 28, wherein the first and second liquid containers and the liquid transfer pump are supported in a drawer of an instrument, wherein the drawer is configured to be laterally movable between an open position providing access to one or more of the first and second liquid containers and the liquid transfer pump and a closed position concealing the first and second liquid containers and the liquid transfer pump.

Embodiment 30. The system of any one of embodiment 19 to 25, wherein the first and second liquid containers and the liquid transfer pump are supported in a drawer of an instrument, wherein the drawer is configured to be laterally movable between an open position providing access to one or more of the first and second liquid containers and the liquid transfer pump and a closed position concealing the first and second liquid containers and the liquid transfer pump, and wherein the connector interface is affixed to the drawer.

Embodiment 31. The system of any one of embodiments 2 to 7, wherein the first liquid container comprises: an intermediate top wall; a liquid inlet tower extending above the intermediate top wall; a liquid inlet fluidly connected to the liquid inlet tower at a position above the intermediate top wall and through which the first liquid container receives liquid from the liquid source; and a vacuum tower extending above the intermediate top wall, wherein the pressure differential source is connected to the vacuum tower at a position above the intermediate top wall.

Embodiment 32. A method for managing liquid waste, the method comprising: a) receiving liquid from a liquid source into a first liquid container; b) monitoring the amount of liquid in the first liquid container; c) connecting a second liquid container to a liquid transfer pump that is connected to the first liquid container by lowering a first connector fitting of the second liquid container into connective engagement with a second connector fitting coupled to an outlet of the liquid transfer pump; d) after the amount of liquid received into the first liquid container reaches a predefined level, as determined in step b), transferring liquid from the first liquid container into the second liquid container with the liquid transfer pump; and e) removing liquid transferred to the second liquid container during step d).

Embodiment 33. The method of embodiment 32, wherein step e) comprises transferring liquid from the second liquid container to a drain with a drain pump fluidly connected to the second liquid container.

Embodiment 34. The method of embodiment 33, wherein step e) further comprises monitoring a liquid level within the second liquid container with a second float switch, generating a pump activation signal when the second float switch detects that the amount of liquid within the second liquid container reaches a predefined level, and transmitting the pump activation signal to the drain pump to activate the drain pump and transfer liquid from the second liquid container to the drain.

Embodiment 35. The method of embodiment 32, further comprising, prior to step e), deactivating the liquid transfer pump.

Embodiment 36. The method of embodiment 35, wherein step e) comprises pouring liquid from the second liquid container through an opening in the second liquid container.

Embodiment 37. The method of embodiment 35 or 36, wherein steps a) and e) occur simultaneously.

Embodiment 38. The method of any one of embodiments 35 to 37, wherein the first and second liquid containers and the liquid transfer pump are supported in a drawer of an instrument, wherein the drawer is configured to be laterally movable between an open position providing access to one or more of the first and second liquid containers and the liquid transfer pump and a closed position concealing the first and second liquid containers and the liquid transfer pump, and wherein step e) further comprises laterally moving the drawer to the open position and removing the second liquid container from the drawer after deactivating liquid transfer pump.

Embodiment 39. The method of any one of embodiments 32 to 38, wherein the first connector fitting comprises a male fitting extending downwardly from the second liquid container, and the second connector fitting comprises an upwardly facing female fitting and configured to receive the male fitting.

Embodiment 40. The method of any one of embodiments 32 to 39, wherein:

step b) comprises monitoring a liquid level within the first liquid container with a float switch; and step c) comprises: generating a pump activation signal when the float switch detects that the amount of liquid within the first liquid container reaches the pre-defined level; and transmitting the pump activation signal to the liquid transfer pump to activate the liquid transfer pump and transfer liquid from the first liquid container to the second liquid container.

Embodiment 41. The method of any one of embodiments 32 to 40, further comprising, after step d) and before step e), drawing liquid from the connection between the first connector fitting and the second connector fitting into the first liquid container.

Embodiment 42. A liquid container system comprising a liquid container, wherein the liquid container comprises: an intermediate top wall; a liquid inlet tower extending above the intermediate top wall; a liquid inlet fluidly connected to the liquid inlet tower at a position above the intermediate top wall and through which the liquid container receives liquid from a liquid source; and a vacuum tower extending above the intermediate top wall and to which a pressure differential source can be fluidly connected at a position above the intermediate top wall to draw liquid into the liquid container through the liquid inlet.

Embodiment 43. The liquid container system of embodiment 42, further comprising a filter in fluid communication with the vacuum tower of the liquid container.

Embodiment 44. The liquid container system of embodiment 43, further comprising a mounting block on which the filter and the liquid container are mounted.

Embodiment 45. The liquid container system of embodiment 44, further comprising a filter loop fluidly connecting the vacuum tower of the liquid container to a bottom portion of the filter supported on the mounting block.

Embodiment 46. The liquid container system of any one of embodiments 42 to 45, further comprising a liquid level sensor configured to detect a liquid level within the liquid container.

Embodiment 47. The liquid container system of embodiment 46, wherein the liquid level sensor comprises a float switch extending into an interior of the liquid container from a float switch connector mounted to the intermediate top wall.

Embodiment 48. The liquid container system of any one of embodiments 42 to 47, further comprising a transfer fitting mounted in the intermediate top wall with a tube extending from the transfer fitting into an interior of the liquid container.

Embodiment 49. The liquid container system embodiment 42, further comprising: a transfer line fitting mounted in the intermediate top wall with a tube extending from the transfer line fitting into an interior of the liquid container; a transfer pump fluidly connected to the transfer fitting; and a transfer container fluidly connected to the transfer pump.

Embodiment 50. The liquid container system of embodiment 49, further comprising a liquid level sensor configured to detect a liquid level within the liquid container, the liquid level sensor being in operative communication with the transfer pump to activate the transfer pump to transfer an amount of liquid from the liquid container to the transfer container when the liquid level sensor detects that the liquid level within the liquid container has reached a prescribed level.

Embodiment 51. The liquid container system of embodiment 46 or 50, further comprising a transfer container interface configured to releasably connect the transfer container to the transfer pump.

Embodiment 52. The liquid container system of embodiment 49, wherein the transfer container comprises: a main body; a connector shelf extending laterally from the main body and including a horizontal portion and defining a bottom wall; and a liquid transfer connector fitting extending downwardly from the bottom wall of the horizontal portion of the connector shelf and configured for fluidly connecting the transfer container to the liquid transfer pump.

Embodiment 53. The liquid container system of embodiment 52, wherein the liquid transfer connector fitting comprises a nipple that extends downwardly from the horizontal portion of the connector shelf and a liquid channel extending through the liquid transfer connector fitting.

Embodiment 54. The liquid container system of embodiment 53, further comprising a transfer container interface configured to releasably connect the transfer container to the transfer pump, the transfer container interface including an upwardly facing receptor opening configured to receive the nipple of the liquid transfer connector fitting.

Embodiment 55. The liquid container system of embodiment 54, wherein the transfer container interface includes a liquid trough, and the receptor opening is disposed within the liquid trough.

Embodiment 56. The liquid container system of any one of embodiments 53 to 55, further comprising one or more O-rings disposed on the nipple.

Embodiment 57. The liquid container system of any one of embodiments 52 to 56, wherein the transfer container further comprises a cap removably secured to an opening formed in the main body of the transfer container, wherein the opening is configured for emptying the contents of the transfer container after removing the cap.

Embodiment 58. The liquid container system of any one of embodiments 52 to 57, wherein the transfer container further comprises a handle secured to the main body.

Embodiment 59. A liquid container system comprising a transfer container for receiving liquid transferred to the transfer container by a liquid transfer pump, wherein the transfer container comprises: a main body; a connector shelf extending laterally from the main body and including a horizontal portion and defining a bottom wall; and a liquid transfer connector fitting extending downwardly from the bottom wall of the horizontal portion of the connector shelf and configured for fluidly connecting the transfer container to the liquid transfer pump.

Embodiment 60. The liquid container system of embodiment 59, wherein the liquid transfer connector fitting comprises a nipple that extends downwardly from the horizontal portion of the connector shelf and a liquid channel extending through the liquid transfer connector fitting.

Embodiment 61. The liquid container system of embodiment 60, further comprising a transfer container interface configured to releasably connect the transfer container to the transfer pump, the transfer container interface including an upwardly facing receptor opening configured to receive the nipple of the liquid transfer connector fitting.

Embodiment 62. The liquid container system of embodiment 61, wherein the transfer container interface includes a liquid trough, and the receptor opening is disposed within the liquid trough.

Embodiment 63. The liquid container system of any one of embodiments 59 to 62, further comprising one or more O-rings disposed on the nipple.

Embodiment 64. The liquid container system of any one of embodiments 59 to 63, wherein the transfer container further comprises a cap removably secured to an opening formed in the main body of the transfer container, wherein the opening is configured for emptying the contents of the transfer container after removing the cap.

Embodiment 65. The liquid container system of any one of embodiments 59 to 64, wherein the transfer container further comprises a handle secured to the main body.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. A liquid container system comprising:

a liquid container, wherein the liquid container comprises (i) an intermediate top wall, (ii) a liquid inlet tower extending above the intermediate top wall, (iii) a liquid inlet fluidly connected to the liquid inlet tower at a position above the intermediate top wall and through which the liquid container receives liquid from a liquid source, and (iv) a vacuum tower extending above the intermediate top wall and including a vacuum fitting configured for attaching a vacuum pump to the vacuum tower at a position above the intermediate top wall to draw liquid into the liquid container through the liquid inlet;

a transfer fitting mounted in the intermediate top wall with a tube extending from the transfer fitting into an interior of the liquid container;

a transfer pump fluidly connected to the transfer fitting; and a transfer container fluidly connected to the transfer pump, wherein the transfer container comprises (i) a main body, (ii) a connector shelf extending laterally from the main body and including a horizontal portion and defining a bottom wall, and (iii) a liquid transfer connector fitting extending downwardly from the bottom wall of the horizontal portion of the connector shelf and configured for fluidly connecting the transfer container to the liquid transfer pump.

2. The liquid container system of claim 1, further comprising a filter in fluid communication with the vacuum tower of the liquid container.

3. The liquid container system of claim 2, further comprising a mounting block on which the filter and the liquid container are mounted.

4. The liquid container system of claim 3, further comprising a filter loop fluidly connecting the vacuum tower of the liquid container to a bottom portion of the filter supported on the mounting block.

5. The liquid container system of claim 1, further comprising a liquid level sensor configured to detect a liquid level within the liquid container.

6. The liquid container system of claim 5, wherein the liquid level sensor comprises a float switch extending into an interior of the liquid container from a float switch connector mounted to the intermediate top wall.

7. The liquid container system of claim 1, further comprising a liquid level sensor configured to detect a liquid level within the liquid container, the liquid level sensor being in operative communication with the transfer pump to activate the transfer pump to transfer an amount of liquid from the liquid container to the transfer container when the liquid level sensor detects that the liquid level within the liquid container has reached a prescribed level.

8. The liquid container system of claim 1, wherein the liquid transfer connector fitting comprises a nipple that extends downwardly from the horizontal portion of the connector shelf and a liquid channel extending through the liquid transfer connector fitting.

9. The liquid container system of claim 8, further comprising a transfer container interface configured to releasably connect the transfer container to the transfer pump, the transfer container interface including an upwardly facing receptor opening configured to receive the nipple of the liquid transfer connector fitting.

10. The liquid container system of claim 9, wherein the transfer container interface includes a liquid trough, and the receptor opening is disposed within the liquid trough.

11. The liquid container system of claim 8, further comprising one or more O-rings disposed on the nipple.

12. The liquid container system of claim 1, wherein the transfer container further comprises a cap removably secured to an opening formed in the main body of the transfer container, wherein the opening is configured for emptying the contents of the transfer container after removing the cap.

13. The liquid container system of claim 1, wherein the transfer container further comprises a handle secured to the main body.

14. The liquid container system of claim 1, further comprising a vacuum pump connected to the vacuum fitting.

* * * * *